United States Patent
Nunoshige et al.

(10) Patent No.: US 9,771,436 B2
(45) Date of Patent: Sep. 26, 2017

(54) METHOD FOR FORMING POLYMER USING BORON COMPOUND, POLYMERIZATION INITIATOR AND THE POLYMER

(75) Inventors: Jun Nunoshige, Tokyo (JP); Takahito Muraki, Tokyo (JP); Hiroyuki Kagawa, Tokyo (JP)

(73) Assignee: HITACHI, LTD., Tokyo (JP)

(*) Notice: Subject to any disclaimer, the term of this patent is extended or adjusted under 35 U.S.C. 154(b) by 212 days.

(21) Appl. No.: 14/420,566

(22) PCT Filed: Sep. 6, 2012

(86) PCT No.: PCT/JP2012/072683
§ 371 (c)(1),
(2), (4) Date: Feb. 9, 2015

(87) PCT Pub. No.: WO2014/038031
PCT Pub. Date: Mar. 13, 2014

(65) Prior Publication Data
US 2015/0307638 A1    Oct. 29, 2015

(51) Int. Cl.
*C08F 4/52* (2006.01)
*C07F 5/02* (2006.01)
(Continued)

(52) U.S. Cl.
CPC .............. *C08F 4/52* (2013.01); *C07F 5/027* (2013.01); *C07F 7/1804* (2013.01); *C09K 3/10* (2013.01);
(Continued)

(58) Field of Classification Search
CPC ........... C08F 4/52; H01B 3/442; H01B 3/447; C09K 3/10; C07F 5/027; C07F 7/1804
(Continued)

(56) References Cited

U.S. PATENT DOCUMENTS 4,167,616 A * 9/1979 Bollinger .................. C08F 4/44
260/665 R

FOREIGN PATENT DOCUMENTS

JP    2001-059007 A    3/2001
JP    2002-194014 A    7/2002
(Continued)

OTHER PUBLICATIONS

Machine translation of Detailed Description of JP 2003-252919A; published Sep. 10, 2003.*
(Continued)

*Primary Examiner* — Fred M Teskin
(74) *Attorney, Agent, or Firm* — Volpe and Koenig, P.C.

(57) ABSTRACT

The present invention provides a method for forming a polymer by using a mixture containing a polymerization initiator which is an adduct of a boron compound and a first unsaturated hydrocarbon compound, and a second unsaturated hydrocarbon compound, generating a radical by oxidization of the polymerization initiator and adding the radical to the second unsaturated hydrocarbon compound, thereby forming the polymer. According to the present invention, excellent controllability of alkylboranes for radical polymerization can be maintained and the structure of a polymerization initiation terminal can be freely selected and controlled. Thus, a terminal-modified polymer having functionality imparted to the terminal group can be prepared. In addition, a polymerization initiator having a plurality of polymerization starting points can be prepared, and polymers with special structures including multibranched polymers, grafted-type (comb-type) polymers and brush-shaped polymers can be prepared.

16 Claims, 5 Drawing Sheets

(51) Int. Cl.
    *C07F 7/18*     (2006.01)
    *C09K 3/10*     (2006.01)
    *H01B 3/44*     (2006.01)
    *C08F 279/02*     (2006.01)

(52) U.S. Cl.
    CPC ............ *H01B 3/442* (2013.01); *H01B 3/447* (2013.01); *C09K 2200/0625* (2013.01); *C09K 2200/0632* (2013.01)

(58) Field of Classification Search
    USPC ........................................................ 526/194
    See application file for complete search history.

(56) References Cited

FOREIGN PATENT DOCUMENTS

| | | |
|---|---|---|
| JP | 2003-252919 A | 9/2003 |
| JP | 2004-083727 A | 3/2004 |
| JP | 2004-331762 A | 11/2004 |
| JP | 2005-330446 A | 12/2005 |
| JP | 2006-348290 A | 12/2006 |
| WO | 2012/137338 A | 10/2012 |

OTHER PUBLICATIONS

Machine translation of Detailed Description of JP 2001-059007A; published Mar. 2001.*

Yang Qin, et al. "Preparation of Organoboron Block Copolymers via ATRP of Silicon and Boron-Functionalized, Monomers", Macromolecules, 2005, vol. 38, 8987-8990.

* cited by examiner (I)

(II)

(III)

METHOD FOR FORMING POLYMER USING BORON COMPOUND, POLYMERIZATION INITIATOR AND THE POLYMER

TECHNICAL FIELD

The present invention relates to a method for forming a polymer using a boron compound, a polymerization initiator and the polymer.

BACKGROUND ART

Borane which is a hydrogen compound of boron is a compound that forms a three-centered two-electron bond using an unoccupied orbital of boron and, in view of its feature, is stabilized by dimerization or formation of a complex with a Lewis basic material. Further, since borane is highly reducing, it acts as a reducing agent, for example, to an unsaturated bond in organic synthesis. In particular, addition reaction to the unsaturated bond is referred to as hydroboration and generally known as a customary method of hydroxylation or coupling reaction.

Further, it has been known that an alkyl borane as a sort of borane compounds generates radicals in a low temperature and oxygen atmosphere and is used also as an initiator for radical polymerization. For example, a method of polymerizing an acrylic monomer using 9-borabicyclo[3,3,1]nonane (9-BBN) as a polymerization initiator (Patent Literature 1) and a method of polymerizing a vinyl compound excluding vinyl acetate using S-alpineborane as a polymerization initiator (Patent Literature 2) are shown. Any of the methods shows a result that a polymerization terminal radical forms dormant species with an alkylborane by using the alkylborane to develop a living radical property. In view of the above, radical polymerization can be performed under excellent polymerization controllability by using an alkylborane type polymerization initiator.

Further, Patent Literature 3 discloses a method of polymerization using borane $BH_3$ as a polymerization initiator for vinylic monomers, and using a complex of $BH_3$ and tetrafuran or a trialkylboron compound under the co-existence of a solvent having etheric oxygen atoms such as tetrahydrofuran, diglyme, dioxane, etc. in the molecular structure thereof in an atmosphere containing 20±5% oxygen, particularly, in atmospheric air.

CITATION LIST

Patent Literature

Patent Literature 1: Japanese Unexamined Patent Application Publication No. 2002-194014
Patent Literature 2: Japanese Unexamined Patent Application Publication No. 2005-330446
Patent Literature 3: Japanese Unexamined Patent Application Publication No. 2004-331762

SUMMARY OF INVENTION

Technical Problem

Polymerization initiators by which proceeding of radical polymerization in an oxygen atmosphere has been confirmed are limited to some alkylboranes as described above, and detailed polymerization behaviors have not yet been known for the systems using other borane compounds. Further, the alkylborane type polymerization initiators reported so far can perform radical polymerization at excellent controllability but, on the other hand, a starting point of radical polymerization (polymerization initiation terminal) is restricted to some alkyl radicals generated by oxidative cleavage of the alkylborane. That is, since the polymerization initiation terminal depends on the alkylborane structure, the polymerization initiation terminal of the polymer cannot be selected optionally in the system using the alkylborane type polymerization initiator.

Accordingly, for new development of a technique for the alkylborane type polymerization initiator of excellent polymerization controllability, the present invention intends to provide a new method for radical polymerization adaptable to manufacture of a polymer having terminal modified group and special structure, an initiator, therewith, a radical polymer and a living radical polymer concerned therewith.

Solution to Problem

The method for forming the polymer according to the present invention has a feature of using a mixture containing a polymerization initiator which is an adduct of a boron compound and a first unsaturated hydrocarbon, and a second unsaturated hydrocarbon compound, generating radicals by oxidation of the polymerization initiator, and adding the radicals to a second unsaturated hydrocarbon compound, thereby forming the polymer.

Advantageous Effects of Invention

According to the present invention, it is possible to maintain the excellent controllability of the alkylborane for radical polymerization and optionally select and control the structure of the polymerization initiation terminal. Thus, a terminal modified polymer having functionality imparted to the terminal group can be prepared. Further, a polymerization initiator having a plurality of polymerization initiation points can be prepared and polymers of special structure, for example, multibranched polymers, grafted (comb-shaped) polymers, and brush-shaped polymers can be prepared.

DESCRIPTION OF EMBODIMENTS

Figure 1:
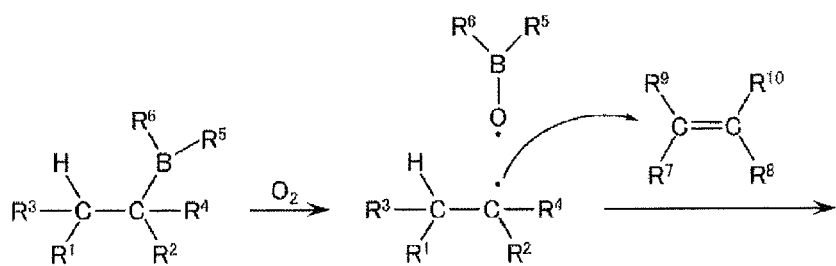
FIG. 1 is a view schematically illustrating a process of forming a polymerization initiator and a polymer according to a present embodiment.
Figure 1:
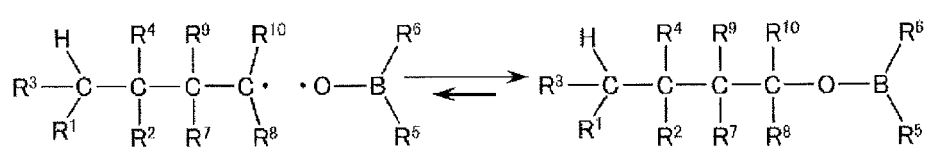
Figure 1:
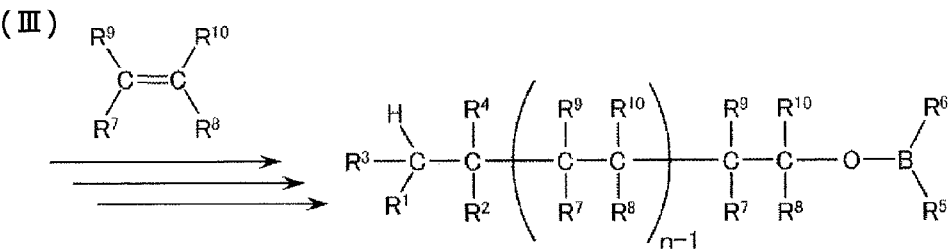

The present invention relates to a method for living radical polymerization by using a boron compound, a polymerization initiator showing a living radical polymerizability, and a polymer synthesized by using the polymerization initiator.

The present inventors have made investigation for the preparation of polymers having terminal modified groups and special structures by a method different from that of the Patent Literature 1 or the Patent Literature 2. As a result, it has newly been found that the selectivity and the controllability of the polymerization initiation terminal are improved outstandingly by adopting a 2-stage reaction including a process for forming an alkylborane initiator by hydroborating reaction between a compound having an unsaturated bond as a polymerization initiation terminal and a boron compound, and a process for adding a monomer component forming the polymer to generate radicals of the polymerization initiator (also referred to simply as "initiator") and radical addition polymerization in an oxygen atmosphere, to accomplish the present invention.

A method for forming a polymer, a polymerization initiator, and a polymer according to an embodiment of the present invention are to be described.

The method for forming the polymer has a feature in using a mixture containing a polymerization initiator which is an adduct of a boron compound and a first unsaturated hydrocarbon compound and a second unsaturated hydrocarbon compound, generating radicals by oxidation of the polymerization initiator, and adding the radicals to the second unsaturated hydrocarbon compound, thereby forming the polymer.

The first unsaturated hydrocarbon compound means an unsaturated hydrocarbon compound as a starting material for the polymerization initiator. The second unsaturated hydrocarbon compound means an unsaturated hydrocarbon compound as a starting material for the main chain of the polymer.

In the method for forming the polymer, the boron compound is preferably borane, methylborane, isopropylborane, 1-butylborane, sec-butylborane, tert-butylborane, isopinocampheylborane, dimethylborane, disiamylborane, diisopinocampheylborane, or bicyclo[3.3.1]nona-9-borane.

In the method for forming the polymer, the molecule of the first unsaturated hydrocarbon compound preferably contains one or more atoms selected from the group consisting of oxygen, nitrogen, phosphorus, sulfur, and halogen and is in a linear, branched, or ring form.

In the method for forming the polymer, the first unsaturated hydrocarbon compound is preferably has at least one molecular structure selected from the group consisting of ether bond, ester bond, urethane bond, amide bond, thioester bond, carbonyl group, carboxyl group, amino group, alkylamino group, dialkylamino group, and pyridyl group.

In the method for forming the polymer, the first unsaturated hydrocarbon compound preferably has at least one molecular structure selected from the group consisting of pyrrolidyl group, isocyanuric acid ester skeleton, cyanuric acid ester skeleton, hexahydrotriazine skeleton, maleimide skeleton, and imidazole skeleton.

In the method for forming the polymer, the first unsaturated hydrocarbon group is preferably an organic silicone compound, an organic titanium compound, or an organic zirconium compound having a linear, branched, or cyclic molecular structure.

In the method for forming the polymer, the molecule of the first unsaturated hydrocarbon compound preferably contains at least two unsaturated hydrocarbon groups.

In the method for forming the polymer, the molecule of the first unsaturated hydrocarbon compound preferably has a configuration having one atom as a center skeleton and at least two unsaturated hydrocarbon groups bonded to the atom.

In the method for forming the polymer, the molecule of the first unsaturated hydrocarbon compound preferably has a cyclic molecular structure as a center skeleton and contains at least two unsaturated hydrocarbon groups on the side chain of the molecular structure.

In the method for forming the polymer, the first unsaturated hydrocarbon group preferably has a linear or branched molecular structure and contains at least two unsaturated hydrocarbon groups in the molecular structure.

In the method for forming the polymer, the first unsaturated hydrocarbon compound is preferably acrylamide, N,N-dimethyl acrylamide, 1-vinyl-2-pyrrolidone, 2-vinylpyridine, methacrylic acid, vinyl triethoxysilane, 3-methacryloxypropyl trimethoxysilane, p-styryl trimethoxysilane, tetraallyl silane, pentaerythritol tetraacrylate, divinylbenzene, diallyl isocyanurate, triallyl isocyanurate, triallylcyanurate, trivinylcyclohexane, trimethylol propane triacrylate, or poly-1,2-butadiene.

In the method for forming the polymer, the second unsaturated hydrocarbon compound is preferably one or more unsaturated monomers selected from the group consisting of aromatic vinyl compound, aromatic vinyl compounds, alkyl (meth)acrylates, unsaturated monocarboxylic acid esters, fluoroalkyl(meth)acrylates, siloxanyl compounds, mono-(meth)acrylate and di-(meth)acrylates of alkylene glycols, alkoxyalkyl(meth)acrylates, cyanoalkyl(meth)acrylates, acryronitrile, methacrylonitrile, oligo(meth)acrylates and, hydroxyalkyl(meth)acrylates of polyhydric alcohols, hydroxyalkyl esters of unsaturated carboxylic acids, monoesters and diesters of unsaturated alcohols, unsaturated (mono)carboxylic acids, unsaturated polycarboxylic acids and unsaturated polycarboxylic acid anhydrides; unsaturated polycarboxylic acids and unsaturated polycarboxylic acid anhydrides, epoxy group-containing unsaturated compounds, diene compounds, vinyl chloride, vinyl acetate, sodium isoprene sulfonate, cinnamic acid esters, crotonic acid esters, dicyclopentadienyl, and ethylidene norbornene.

In the method for forming the polymer, the first unsaturated hydrocarbon compound and the second unsaturated hydrocarbon compound can be different compounds, and a molecular structure of the polymerization initiation terminal of the first unsaturated hydrocarbon compound and the molecular structure of a constituent unit constituting the main chain of the polymer formed by polymerization of the second unsaturated hydrocarbon compound can be different.

The method for forming the polymer preferably includes a step of preparing the polymerization initiator by adding a boron compound to the first unsaturated hydrocarbon compound (polymerization initiator preparation step).

In the method for forming the polymer, the step of preparing the polymerization initiator and the step of forming the polymer are preferably performed by one-pot reaction.

In the method for forming the polymer, the step of forming the polymer is preferably living radical polymerization by the formation of a dormant of the boron compound.

The polymerization initiator is prepared characteristically by addition reaction of the boron compound and the first unsaturated hydrocarbon compound.

The addition reaction of the polymerization initiator is preferably hydroborating reaction.

The polymerization initiator preferably has a function of generating radicals by being oxidized with addition of oxygen and forming radicals which reacts with the second unsaturated hydrocarbon compound to form the polymer.

In the polymerization initiator, the first unsaturated hydrocarbon compound is preferably acrylamide, N, N-dimethyl acrylamide, 1-vinyl-2-pyrrolidone, 2-vinylpyridine, methacrylic acid, vinyl triethoxysilane, 3-methacryloxypropyl trimethoxysilane, p-styryl trimethoxysilane, tetraallylsilane, pentaerythritol tetraacrylate, divinylbenzene, diallyl isocyanurate, triallyl isocyanurate, triallyl cyanurate, trivinylcyclohexane, trimethylol propane triacrylate, or poly-1,2-butadiene.

In the polymerization initiator, the boron compound preferably contains one or more atoms selected from the group consisting of oxygen, nitrogen, phosphorus, sulfur, and halogen, has a linear, branched, or cyclic heteroatom-containing alkyl structure and forms a polymerization initiation terminal radicals containing a heteroatom-containing alkyl group by oxidation.

In the polymerization initiator, the heteroatom-containing alkyl structure preferably contains at least one molecular structure selected from the group consisting of ether bond, ester bond, urethane bond, amide bond, thioester bond, carbonyl group, carboxyl group, amino group, alkylamino group, dialkylamino group, and pyridyl group.

In the polymerization initiation, the heteroatom-containing alkyl structure preferably contains at least one molecular structure selected from the group consisting of pyrrolidyl group, isocyanuric acid ester skeleton, cyanuric acid ester skeleton, hexahydrotriazine skeleton, maleimide skeleton, and imidazole skeleton.

The polymerization initiator comprises a boron compound containing at least one molecular skeleton selected from the group consisting of an organic silicon skeleton, an organic titanium skeleton, and an organic zirconium skeleton having a linear, branched, or cyclic molecular structure and has a function of forming a polymerization initiation terminal radical containing the molecular skeleton by oxidation.

In the polymerization initiator, the first unsaturated hydrocarbon compound preferably contains at least one molecular skeleton selected from the group consisting of ether bond, ester bond, urethane bond, amide bond, thioester bond, carbonyl group, carboxyl group, amino group, alkylamino group, dialkylamino group, pyridyl group, pyrrolidyl group, isocyanuric acid ester skeleton, cyanuric acid ester skeleton, hexahydrotriazine skeleton, maleimide skeleton, and imidazole skeleton, and the boron compound preferably contains at least one molecular skeletons selected from the group consisting of an organic silicon skeleton, an organic titanium skeleton, and an organic zirconium each skeleton having a linear, branched, or cyclic molecular structure and has a function of forming a polymerization initiation terminal radical containing a molecular skeleton by oxidation.

The polymerization initiator comprises a boron compound having at least two or more alkyl borane structures bonded to one atom as a center skeleton and has a function of forming at least two polymerization initiation terminal radicals by oxidation.

The polymerization initiator comprises a boron compound having at least two alkyl borane structures bonded to the side chain of a cyclic molecular structure as a center skeleton and has a function of forming at least two or more polymerization initiation terminal radicals by oxidation.

The polymerization initiator comprises a boron compound having a linear or branched molecular structure as a center skeleton, and having at least two or more alkyl borane structures in the molecular structure, and has a function of forming at least two polymerization initiation terminal radicals by oxidation.

The polymer is preferably prepared from the polymerization initiator and the second unsaturated hydrocarbon compound by the forming method described above.

The polymer comprises a polymerization initiation part, a polymerization terminal part, and a main chain disposed between them, in which at least one molecular structure of the polymerization initiation part and the polymerization terminal part and the molecular structure of the repeating unit forming the main chain may be different.

The polymer comprises a polymerization initiation part, a polymerization terminal part, and a main chain disposed between them, in which at least one molecular structure of the polymerization initiation part and the polymerization terminal part and the molecular structure of the repeating unit forming the main chain may be different, and the boron compound may form a growth terminal group.

The polymer preferably comprises a polymerization initiation part, a polymerization terminal part, and a chain disposed between them and has at least two main chains.

In the polymer, the second unsaturated hydrocarbon compound is preferably one or more unsaturated monomers selected from the group consisting of aromatic vinyl compound, aromatic allyl compounds, heterocycle-containing vinyl compounds, heterocycle-containing allyl compounds, alkyl(meth)acrylates, unsaturated monocarboxylic acid esters, fluoroalkyl(meth)acrylates, siloxanyl compounds, mono-(meth)acrylate and di-(meth)acrylates, alkoxyalkyl(meth)acrylates, cyanoalkyl(meth)acrylates of alkylene glycols, acryronitrile, methacrylonitrile; oligo(meth)acrylate or hydroxyalkyl(meth)acrylates of polyhydric alcohols, hydroxyalkyl esters of unsaturated carboxylic acids, unsaturated alcohols, unsaturated(mono)carboxylic acids, unsaturated polycarboxylic acids, and unsaturated polycarboxylic acid anhydrides; monoesters and diesters of unsaturated polycarboxylic acids or unsaturated polycarboxylic acid anhydrides; epoxy group-containing unsaturated compounds, diene compounds, vinyl chloride, vinyl acetate, sodium isoprene sulfonate, cinnamic acid esters, crotonic acid esters, dicyclopentadienyl, and ethylidene norbornene.

In the polymer, the boron compound preferably forms a growth terminal group.

The polymer preferably comprises a polymerization initiation part, a polymerization terminal part, and a main chain disposed between them, and at least one molecular structure of the polymerization initiation part and the polymer terminal part preferably contains one or more atoms selected from the group consisting of oxygen, nitrogen, phosphorus, sulfur, and halogen and has a linear, branched, or cyclic molecular structure.

The polymer preferably comprises a polymerization initiation part, a polymerization terminal part and a main chain disposed between them, at least one molecular structure of the polymerization initiation part and the polymerization terminal end part contains at least one molecular structure selected from the group consisting of an ether bond, ester bond, urethane bond, amide bond, thioester bond, carbonyl group, carboxyl group, amino group, alkylamino group, dialkylamino group, and pyridyl group.

The polymer preferably comprises a polymerization initiation part, a polymerization terminal part and a main chain disposed between them, and at least one molecular structure of the polymer initiation part and the polymerization terminal part contains at least one molecular structure selected from the group consisting of pyrrolidyl group, isocyanuric acid ester skeleton, cyanuric acid ester skeleton, hexahydrotriazine skeleton, maleimide skeleton, and imidazole skeleton.

The polymer comprises a polymerization initiation part, a polymerization terminal part, and a main chain disposed between them, and at least one molecular structure of the polymerization initiation part and the polymerization terminal part contains at least one molecular structure selected from the group consisting of an organic silicon skeleton, an organic titanium skeleton, and an organic zirconium skeleton each having a linear, branched, or cyclic molecular structure (chained portion, branched portion, or cyclic portion).

The polymer comprises one atom as a center skeleton and at least two chain growth parts bonded to the atom. The chain growing portion means a molecular structure grown linearly by polymerizing reaction.

The polymer comprises one cyclic molecular structure as a center skeleton and at least two chain growth parts bonded to the molecular structure.

The polymer comprises a linear or branched molecular structure and has at least two chain growth parts bonded to the molecular structure.

The polymer may be used for a cable coating member or a mold sealant.

The cable coating member may be used for cable.

The mold sealant may be used for a mold sealing method.

The mold sealant may be used for an electronic part package.

The polymer can be used for a structural material such as casing member, a frame member, a panel member, and a model member.

The polymer preferably contains a polymerization initiation part, a polymerization terminal part, and a main chain disposed between them, in which boron is preferably contained in the polymerization initiation part, the polymerization terminal, or the main chain.

An embodiment for practicing the invention (present embodiment) is to be described later but the present embodiment is not restricted to the following contents, and can be practiced with optional changes within a range not impairing the gist of the invention.

[1. Polymerization Initiator and Manufacturing Method of Polymer]

The polymerization initiator and the polymer according to the present embodiment are formed by way of the following two processes.

(1) A process for preparing a polymerization initiator of forming an adduct of a boron compound by the reaction of adding the boron compound to the unsaturated hydrocarbon compound forming the polymerization initiator (hydroboration)

(2) A polymer forming process of proceeding polymerization by a reaction of adding radicals generated by oxidizing reaction of the polymerization initiator to an unsaturated hydrocarbon compound under the presence of the polymerization initiator and the unsaturated hydrocarbon compound forming the polymer In the present embodiment, the specific method is not restricted particularly so long as the method is practiced by way of the process for preparing the polymerization initiator and the process for forming the polymer. Each of the preparation processes may be practiced by optionally adding one or more solvents, dispersants, stabilizers, catalysts, viscosity controllers, and like other additives. The present embodiment is to be described with reference to the drawings.

FIG. 1 is a view schematically showing a process of forming a polymerization initiator and a polymer according to the present embodiment.

In the drawing, $R^1$ to $R^{10}$ may be identical or different each other. $R^1$ to $R^{10}$ are side chains of a boron compound, an unsaturated hydrocarbon compound forming a polymerization initiator, and an unsaturated hydrocarbon compound forming a polymer. The structure of each of the side chains may be identical or different each other and specific structure is not particularly restricted so long as the structure can be a side chain structure such as hydrogen, a chained structure and a structure cyclized in one identical molecule. The unsaturated hydrocarbon compound forming the polymerization initiator is the first unsaturated hydrocarbon compound described above. Further, the unsaturated hydrocarbon compound forming the polymer is the second unsaturated hydrocarbon compound described above.

In the drawing, reaction proceeds by way of the steps (I) to (III).

In the step (I), a boron compound and an unsaturated hydrocarbon component forming a polymerization initiator form an alkylboron compound by hydroboration.

The alkylboron compound formed by the reaction may possibly generate radicals in an oxygen atmosphere and cause addition polymerization with the unsaturated hydrocarbon compound not completed for the addition reaction. Accordingly, the reaction is preferably practiced in an inert gas atmosphere.

Borane (boron in a narrow sense, that is, monoborane and diborane) or 1-substituted borane compound in which one of $R^6$ and $R^7$ is hydrogen and the other of them is a carbon-containing functional group may sometimes cause hydroboration to other unsaturated hydrocarbon depend on the conditions of the addition reaction or the concentration of borane or the borane compound. While the present embodiment can be practiced with no particular restriction on the state of borane addition, it is more preferred to perform the process while controlling the amount of the borane compound considering the amount of the unsaturated hydrocarbon. Further, since the hydroborated unsaturated hydrocarbon skeleton is transformed by hydroboration into a saturated hydrocarbon bond, it does not undergo radical addition polymerization in itself. Accordingly, the unsaturated hydrocarbon compound forming the polymerization initiator does not form a constituent element of the polymer.

In the step (II), the boron compound and oxygen sealed in the system react to form radical reaction species. It is considered that a portion of the boron compound is cleavaged by oxygen addition to form an oxygen-centered radical containing an alkyl radical and boron. It is more preferred that $R^6$ and $R^7$ are functional groups less undergoing oxidation cleavage than the unsaturated hydrocarbon compound forming the polymerization initiator. Further, for the method of oxidation, known method such as addition of an oxidizer can be used in addition to the method by oxygen addition.

The generated alkyl radical forms a radical adduct by radical addition reaction with an unsaturated hydrocarbon compound forming the polymer. The radical growth terminal of the radical adduct is a highly reactive and unstable terminal group but it is considered that quasi-stable bonding terminal (dormant species) is temporarily formed and stabilized at the radical growth terminal of the radical adduct by the presence of an oxygen-centered radical containing boron. It is considered that while the quasi-stable terminal (bonded body of the radical growth terminal and the oxygen-centered radical containing boron) per se shows no radical polymerizability, but shows a living polymerization behavior by reversibly forming the radical growth terminal in a small amount making it possible for precise control of polymerization.

In step (III), the radical growth terminal reversibly generated from the dormant species causes chained addition reaction with the unsaturated hydrocarbon compound forming the polymer to form a n-multimerized polymer. It is considered that the concentration of the radical growth terminal concerned with polymerization is extremely lower than the concentration of the dormant species and side reaction as in usual radical polymerization (termination reaction such as recombination, dispropornation, and chain transfer) is suppressed.

Further, assuming that the inter-exchange between the radical growth terminal and the dormant is sufficiently fast, since respective dormant species are converted to radical growth terminals substantially at an identical probability, they are grown into a polymer of uniform chain length. Thus, for example, control for the molecular weight and the molecular weight distribution and formation of a block type copolymer can be realized. Further, while the polymerizing reaction proceeds in any of inert gas atmospheres such as nitrogen or argon and oxygen-containing air, since oxygen sometimes acts for deactivation of dormant species or as a polymerization inhibitor in a system where oxygen is present in an excess amount, the polymerization is more preferably performed in an inert gas atmosphere.

In the present embodiment, a polymer can be formed by selecting a molecular structure containing atoms other than carbon and hydrogen with an aim of imparting functionality to the polymerization initiation terminal group. For example, an operative functional group containing an organic compound having a heteroatom such as oxygen, nitrogen, and sulfur, or an organic silane compound, organic titanium compound, or an organic zirconium compound can be provided. The structure of the polymerization initiation terminal is a functional group containing a linear, branched, or cyclic molecular structure and the specific structure and bonding site of the unsaturated bond are not particularly restricted so long as the structure can be formed by the method.

Figure 2:
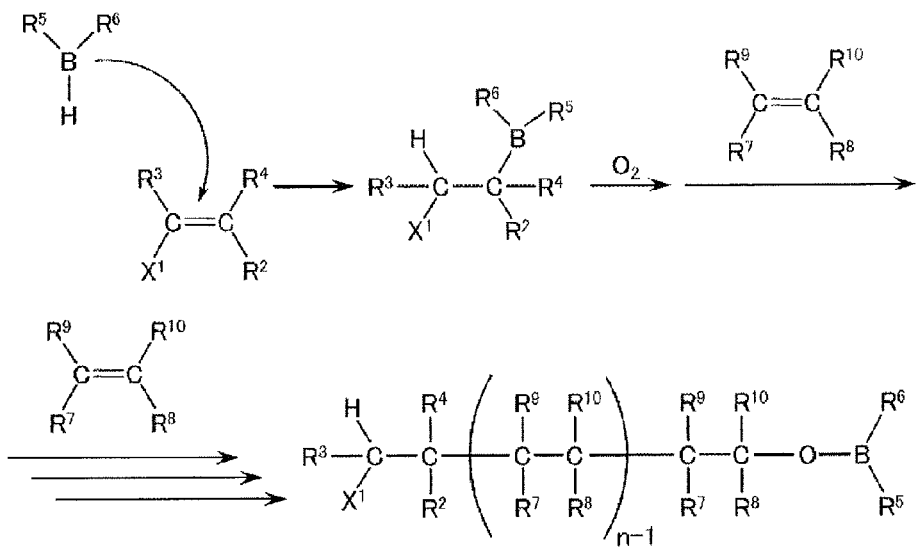
FIG. 2 is a view schematically illustrating a method for forming a polymerization initiator and a polymer according to the present embodiment.

FIG. 2 is a view schematically illustrating an example of a process for forming a polymerization initiator and a terminal modified polymer according to the embodiment.

In the drawing, $R^2$ to $R^{10}$ may be identical or different each other.

$R^2$ to $R^{10}$ are side chains of a boron compound, an unsaturated hydrocarbon group forming the polymerization initiator, and an unsaturated hydrocarbon compound forming the polymer. $X^1$ is the operative functional group described above.

Figure 3:
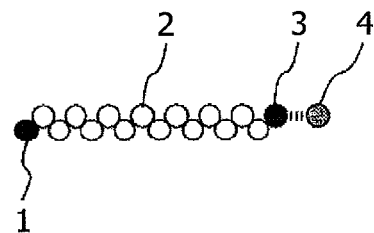
FIG. 3 is a view schematically illustrating an example of a terminal modified polymer according to the present embodiment.

Further, FIG. 3 is a view schematically illustrating an example of a terminal modified polymer according to the present embodiment.

In the polymerization technique using the existent alkylborane polymerization initiator, since polymerization proceeds by oxidation of the initiator, it is difficult to form a terminal modified structure selection with the one-molecule terminal group as the initiation point as in the present embodiment. The terminal modified polymer can be formed by polymerization while separating the process for preparing the polymerization initiator and the process for forming the polymer as in the present embodiment.

In the present embodiment, a multibranched polymer corresponding to or similar with that in this drawing can be prepared by using one of functional groups of the unsaturated hydrocarbon forming the polymerization initiator as a terminal modified group.

As illustrated in the drawing, the radical polymer comprises a polymerization initiation part 1 which is a polymerization initiation part forming the polymerization initiator and a radical polymer part 2. Further, dormant species comprising a radical polymerization terminal 3 and an oxygen-centered radical 4 containing boron (growth terminal group) is formed at the polymerization terminal of the radical polymer 2. In the radical polymer part 2, the unsaturated hydrocarbon compound as the monomer is bonded by radical polymerization starting from the polymer initiation part 1 as a starting point, which forms a linear single bond to form the skeleton of the molecule of the radical polymer.

It is considered that the radical polymer (polymer) is grown by living radical polymerization. Further, random copolymerization and block copolymerization can be conducted optionally using unsaturated hydrocarbon compounds forming a plurality of polymers and controlling the polymerizing conditions.

Further, in the present embodiment, a multi-functional unsaturated hydrocarbon compound containing at least two unsaturated hydrocarbon groups can be used for the unsaturated hydrocarbon compound forming the polymerization initiator. For the multifunctional unsaturated hydrocarbon compound, the structure and the bonding site of the unsaturated hydrocarbon group and the structure of the monomer are not particularly restricted so long as the unsaturated monomer can cause addition reaction with the borane compound. By using the unsaturated monomer having a plurality of polymerization initiation points, polymers of special structures such as a multibranched polymer, a grafted polymer, or a brush-shape a polymer can be prepared. Such structure can be selected optionally depending on the structure of the unsaturated monomer.

The polymerization initiation terminal/polymerization start site to which the unsaturation hydrocarbon is bonded has a linear, branched, or cyclic molecular structure. Specific structure, bonding position of the unsaturated bond, and the number of bonds of the unsaturated bonds contained in the molecule are not particularly restricted so long as the structure can be formed by the polymerization described above. Further, the structures of the unsaturated hydrocarbon groups may be different.

Figure 4:
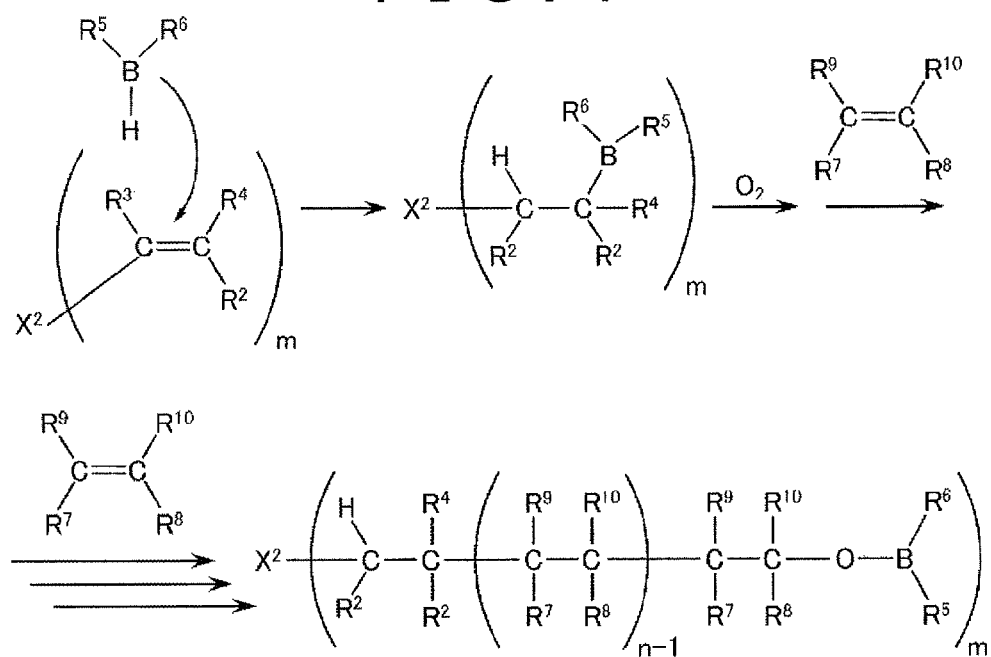
FIG. 4 is a view schematically illustrating an example of a method for forming a polymerization initiator and a multibranched polymer according to the present embodiment.

FIG. 4 is a view schematically illustrating a method for forming a polymerization initiator and a multibranched polymer according to the present embodiment.

In the drawing, $R^2$ to $R^{10}$ may be identical with or different from each other. The $R^2$ to $R^{10}$ are side chains of the boron compound, the unsaturated hydrocarbon compound forming the polymerization initiator, and the unsaturated hydrocarbon compound forming the polymer. $X^2$ is a multifunctional unsaturated hydrocarbon group.

Figure 5A:
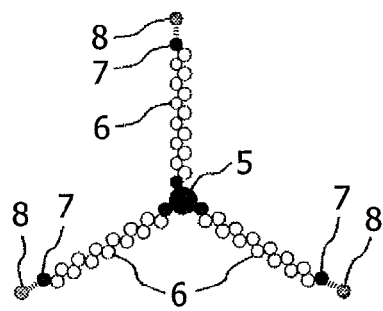
FIG. 5A is a view schematically illustrating an example of a multibranched polymer according to the present embodiment.
Figure 5B:
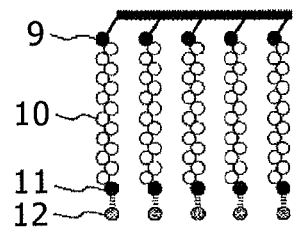
FIG. 5B is a view schematically illustrating an example of a grafted polymer according to the present embodiment.
Figure 5C:
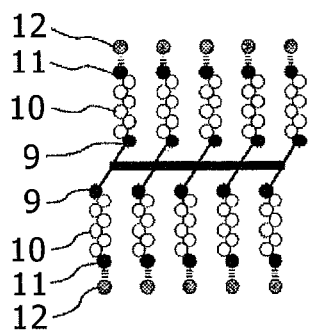
FIG. 5C is a view schematically illustrating an example of a brush-shaped polymer according to the present embodiment.

FIGS. 5A to 5C are views schematically illustrating examples of multibranched polymers according to this embodiment.

In the polymerization technique using the existent alkylborane polymerization initiator, since polymerization proceeds by oxidation of the initiator, it is difficult to form a multibranched structure starting from the multifunctional monomer as in the present embodiment. On the contrary, in the present embodiment, the multibranched polymer can be formed by conducting polymerization while separating the process for preparing the polymerization initiator and the process for forming the polymer.

FIG. 5A illustrates an example of a multibranched polymer of conducting polymerization by a polymerization initiator of a molecular structure having three polymerization initiation points.

In the drawing, a multibranched polymer corresponding to or similar with that in the drawing can be prepared by using a multifunctional compound forming a polymerization initiator having one atom or a cyclic molecular structure as a center skeleton and containing at least two unsaturated hydrocarbon groups.

The radical polymer illustrated in the drawing comprises a polymerization initiation terminal 5 as a polymerization initiation site forming the polymerization initiator, and a radical polymer part 6. Further, a dormant species comprising a radical polymer terminal 7 and a boron-containing oxygen-centered radical 8 is formed at the polymerization terminal of the radical polymer part 6. In the radical polymer part 6, unsaturated hydrocarbon compounds as the monomers are bonded by radical polymerization starting from the functional group of the polymerization initiation terminal 5 and form a chained single bond to form a molecular skeleton of the radical polymer. It is considered that the radical polymer (polymer) is grown by living radical polymerization. Further, random copolymerization and block copolymerization can be conducted optionally by using a plurality of unsaturated hydrocarbon compounds forming the polymers and controlling the polymerization conditions.

Further, FIG. 5B illustrates a grafted polymer polymerized by using a polymerization initiator having five polymerization initiation points. FIG. 5C illustrates a brush-shape a polymer having ten polymerization initiation points.

In the drawings, multibranched polymers corresponding to or similar with those of the schematic views can be prepared by using a multifunctional compound having a linear or branched molecular structure and containing at least two unsaturated hydrocarbon groups in the molecular structure.

The radical polymer illustrated in FIG. 5B contains five polymerization initiation terminals 9 which are linear or branched polymerization initiation sites forming the polymerization initiator, and five radical polymer parts 10. Further, dormant species each comprising a radical polymer terminal 11 and a boron-containing oxygen-center radical 12 are formed at the polymerization terminals of radical polymer parts 10. In the radical polymerization parts 10, unsaturated hydrocarbon compounds as the monomers are bonded by radical polymerization starting from the polymerization initiation terminal 9, and form linear single bonds to form the molecular skeleton of the radical polymer.

Also the radical polymer illustrated in FIG. 5C has a configuration similar to that illustrated in FIG. 5B and contains ten polymerization initiation terminals 9 and ten radical polymer parts 10.

It is considered that also the radical polymers (polymers) are grown by living radical polymerization in the same manner as in FIG. 5A. Further, random copolymerization and block copolymerization can be performed optionally by using a plurality of unsaturated hydrocarbon groups forming the polymer and controlling the polymerization conditions.

The weight average molecular weight (Mw) of the polymers is preferably 500 to 200,000, more preferably, 2,000 to 100,000 and, most preferably, 3,000 to 80,000. The poly dispersity of the polymer (Mw/Mn) is preferably 1 to 5 and, more preferably, 1 to 3. When the weight average molecular weight (Mw) of the polymer is within such a range, moldability, solubility, and film depositability of the polymer are excellent and a polymer of excellent processability can be obtained. Further, the molecular weights can be determined by known methods such as gel permeation chromatography, multiangle light scattering method, and viscosity measurement, which can be properly selected depending on the structure of the polymer.

[2. Raw Material]
(1. Borane Compound)

For the borane compound according to this embodiment, specific type thereof is not particularly restricted so long as this is a compound causing hydroboration to an unsaturated hydrocarbon. The borane compound usable in this embodiment is represented by the following general formula (1).

[Chem. 1]

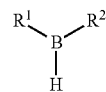

General formula (1)

In the formula, B represents boron and H represents hydrogen. $R^1$ and $R^2$ may be identical or different each other, which is hydrogen, an alkyl group or alkoxy group, or a functional group containing carbon, hydrogen, oxygen, or nitrogen.

Specifically, the borane compound includes, for example, borane (monoborane, diborane), monoalkylborane, dialkylborane, monoalkoxyborane, and dialkoxyborane. However, as the radical polymerization initiator usable in this embodiment, borane, monoalkylborane and dialkylborane are particularly preferred. They may be used alone or may be used in a state properly dissolved or dispersed in a solvent. Further, the borane and borane compound are often instable in itself due to the reactivity thereof. Accordingly, a Lewis basic material or a compound which is stabilized by forming a complex or a salt in a solvent may also be used.

The present embodiment has a feature of obtaining a polymerization initiator by way of hydroboration, which can be attained by using the boron compound represented by the general formula (1) described above.

The alkylborane is not particularly restricted so long as hydroboration is possible and includes, for example, borane complexes such as borane-tetrahydrofuran complex, borane pyridine complex, borane-trimethylamine complex, borane-triethylamine complex, and borane-triemthylphosphine complex, alkylboranes such as methylborane, isopropylborane, 1-butylborane, sec-butylborane, tert-butylborane, and isopinocampheyl borane, and complexes thereof, and dialkylboranes such as dimethylborane, disiamylborane, diisopinocampheylborane, and bicyclo[3.3.1]nona-9-borane (9-BBN) and complexes thereof. They are properly selected while considering the structure and the reactivity of the unsaturated hydrocarbon for which hydroboration is applied and the stability of the dormant species, and plural kinds of them may also be used. Further, they may be substituted with one or more optional substituents. In addition, it may be possible to properly add a catalyst ingredient such as transition metal catalyst, oxide catalyst, and organic compound catalyst with an aim of improving the reactivity, and solvent, dispersant, and stabilizer with an aim of improving the stability of the borane compound.

It has been known that the borane compound has anti-Markovnikov type regioselectivity in the hydroboration. Generally, a borane compound having a more bulky functional group on the side chain has higher regioselectively and the regioselectivity is lower in the compound not having the side chain functional group such as a borane complex. Further, depending on the kind of the unsaturated hydrocarbon compound for hydroboration, a polymer having an asymmetric atom at the polymerization initiation terminal can be prepared and, further, one of optical isomers can be prepared selectively by properly selecting the molecular structure of the side chain of the borane compound.

(2-1. Initiator Unsaturated Hydrocarbon Compound (1))

The unsaturated monomer forming the polymerization initiator according to the present embodiment is not particularly restricted so long as this is an unsaturated monomer having an unsaturated bond and capable of addition reaction (hydroboration) with a borane compound. That is, the polymerization initiator according to the present embodiment is obtained by radical polymerization of an optional known unsaturated monomer capable of hydroboration.

In the present specification, "unsaturated monomer forming the polymerization initiator" represents an unsaturated monomer forming a polymerization initiator when an unsaturated monomer and a borane compound form the polymerization initiator by hydroboration. The unsaturated monomer forms a polymerization initiation terminal for radical polymerization by oxygen addition after the hydroboration.

The unsaturated monomer includes, for example, unsaturated monomers of low molecular weight having a radically polymerizable functional group such as a vinyl group, and polymerizable unsaturated monomers of relatively high molecular weight such as unsaturated polyesters, epoxy vinyl esters, and polybutadienes. Further, for example, monofunctional unsaturated monomers not forming a cross-linked structure by themselves and multifunctional unsaturated monomers having a plurality of polymerization reactive sites referred to as crosslinkers may also be used, and there is no particular restriction also for the structure of the unsaturated monomers.

Specific examples of the unsaturated monomers include aromatic vinyl compounds such as styrene, α-methylstyrene, o-methylstyrene, m-methoxy styrene, o-chlorostyrene, m-chlorostyrene, N,N-dimethyl-p-amino styrene, and divinylbenzene; alkyl(meth)acrylates such as methyl(meth) acrylate, ethyl(meth)acrylate, n-propyl acrylate, n-butyl acrylate, 2-ethylhexyl(meth)acrylate, and stearyl(meth)acrylate; unsaturated monocarboxylic acid esters such as methyl crotonate, ethyl crotonate, methyl cinnamate, and ethyl cinnamate; fluoroalkyl(meth)acrylates such as trifluoroethyl (meth)acrylate, pentafluoropropyl(meth)acrylate, and heptafluorobutyl(meth)acrylate; siloxanyl compounds such as trimethyl siloxanyl dimethyl silyl propyl(meth)acrylate, tris (trimethylsiloxanyl)silylpropyl(meth)acrylate, and di(meth)acryloyl propyl dimethylsilyl ether; monomers or di-(meth)acrylates of alkylene glycols such as ethylene glycol, 1,2-propanediol, 1,3-propanediol, and 1,6-hexanediol; alkoxyalkyl(meth)acrylates such as 2-methoxyethyl(meth) acrylate, 2-ethoxyethyl(meth)acrylate, and 3-ethoxypropyl (meth)acrylate; cyano compounds such as cyanoalkyl(meth) acrylates, for example, cyanoethyl(meth)acrylate and cyanopropyl(meth)acrylate, acrylonitrile, and methacrylonitrile; oligo(meth)acrylates of polyhydric alcohols, for example, di(meth)acrylates, tri(meth)acrylates, or tetra(meth)acrylates of polyhydric alcohols such as glycerin, 1,2, 4-butane triol, pentaerythritol, trimethylol alkanes (number of carbon atoms in the alkane is, for example, 1 to 3), tetramethylol alkane (number of carbon atoms in the alkane is, for example, 1 to 3), hydroxyl alkyl(meth)acrylates such as 2-hydroxyethyl(meth)acrylate, 2-hydroxypropyl(meth) acrylate, and 3-hydroxypropyl(meth)acrylate; hydroxyl alkyl esters of unsaturated carboxylic acids such as 2-hydroxyethyl crotonate, 2-hydroxypropyl crotonate, and 2-hydroxypropyl cinnamate; unsaturated alcohols such as (meth) allyl alcohol; unsaturated (mono)carboxylic acids such as (meth)acrylic acid, crotonic acid, and cinnamic acid; unsaturated polycarboxylic acids (anhydrides) such as (anhydrous) maleic acid, fumaric acid, (anhydrous)itaconic acid; and citraconic acid; and mono or diesters thereof; epoxy group-containing unsaturated compounds such as allyl glycidyl ether and glycol(meth)acrylate; diene compounds such as butadiene, and isoprene; vinyl chloride, vinyl acetate, sodium isoprene sulfonate, cinnamic acid esters, crotonic acid esters, dicyclopentadiene, and ethylidene norbornene.

Among them, preferred examples of unsaturated monomers applicable to the resin material according to the present embodiment include: aromatic vinyl compounds, alkyl (meth)acrylates, unsaturated monocarboxylic acid esters, poly-1,2-butadiene, fluoroalkyl(meth)acrylates, siloxanyl compounds, mono(meth)acrylate, di-(meth)acrylates, alkoxyalkyl(meth)acrylates, cyanoalkyl(meth)acrylates of alkylene glycol, acrylonitrile and methacrylnitrile; oligo (meth)acrylate and hydroxyalkyl(meth)acrylate of polyhydric alcohols; hydroxyalkyl esters of unsaturated carboxylic acids; unsaturated alcohols, unsaturated(mono)carboxylic acids, unsaturated polycarboxylic acids, unsaturated polycarboxylic acid anhydrides, monoesters and diesters of unsaturated polycarboxylic acid, and unsaturated polycarboxylic acid anhydrides; epoxy group-containing unsaturated compounds, dienic compounds, vinyl chloride, vinyl acetate, sodium isoprene sulfonate, cinnamic acid esters, crotonic acid esters, dicyclopentadienyl, and ethylidene norbornene.

(2-2. Initiator Unsaturated Hydrocarbon Compound (2))

Monomers having atoms other than carbon and hydrogen, that is, heteroatoms may also be used with an aim of imparting functionality to the polymerization initiation terminal group. A polar structure can be provided to the polymerization initiation terminal group by introduction of hetero elements and terminal modified polymers that cannot be obtained by existent alkylborane polymerization can be obtained.

As examples of the heteroatoms contained in the structure, one or more atoms selected from the group consisting of nitrogen, oxygen, phosphorus, sulfur, selenium and tellurium are preferred and nitrogen, oxygen or sulfur are more preferred. Such heteroatoms are typical elements having higher electric negativity than that of carbon, which are atoms capable of inducing hydrophilic interaction by way of a hydrophilic structure, hydrogen bond, etc. Examples of such polar structures include a heterocyclic ring containing the heteroatom.

The heterocyclic rings have no particular restriction so long as they are heterocyclic rings satisfying the conditions described above and include, for example, ester bond, urethane bond, amide bond, thioester bond, tetrahydrofuran ring, furan ring, carboxyl group, amino group, alkylamino group, and dialkylamino group.

Specific examples of the unsaturated monomers used herein include, for example, acrylic acid, methacrylic acid, itaconic acid, maleic acid, fumaric acid, glycidylmethacrylate, vinyl pyridine, diethylaminoethyl acrylate, N-methyl methacrylamide, acrylonitrile, acrylamide, N-(hydroxymethyl) acrylamide, and N,N-dimethylacrylamide.

(2-3. Initiator Unsaturated Hydrocarbon Group (3))

As another method of imparting the functionality to the polymerization terminal group, a polar structure can be provided to the polymerization terminal group by introducing a heterocyclic ring containing a plurality of heteroatoms in the ring structure and a terminal modified polymer that cannot be obtained by the existent alkyllborane polymerization can be obtained.

The heterocyclic ring has no particular restriction so long as the heterocyclic ring satisfies the conditions described above and, for example, a 5-membered ring or 6-membered heterocyclic ring, for example, azole ring, triazole ring, tetrazole ring, diazine ring, triazine ring, and tetrazine rings are preferred and 6-membered heterocyclic ring are more preferred. Specific examples of the heterocyclic ring structure include, lactam structure, imidazole ring, imidazoline ring, imidazolidine ring, pyrazole ring, pyrazoline ring, pyrazolidine ring, pyridine ring, oxazole ring, oxazoline ring, oxazolidine ring, isooxazole ring, isooxazoline ring, isooxazolidine ring, triazole ring, thiazoline ring, thiazolidine ring, isothiazole ring, isothiazoline ring, isothiazolidine ring, tetrazole ring, selenazole ring, furazan ring, sydnone ring, urazole ring, guanazole ring, pyrazine ring, piperazine ring, pyrimidine ring, pyridazine ring, morpholine ring, selenomorpholine ring, thiomorpholine ring, triazine ring, quinazoline ring, phthalazine ring, pteridine ring, benzodiazepine ring, benzimidazole ring, purine ring, phenoxazine ring, phenothiazine ring, porphyrin ring, chlorin ring, and colin ring and the like. Derivatives containing the functional groups therein may also be used.

More preferred examples are derivatives containing heteroatoms of high electric negativity such as carbonyl group in the heterocyclic ring. By containing them, the polarity and the hydrophilicity of the heterocyclic ring are enhanced more and the interaction with the hydrophilic structure is improved further. Further, the heterocyclic ring can be modified properly in accordance with the solute as an object of adsorption.

Specific examples of the unsaturated monomer used herein include, for example, 1-vinyl-2-pyrrolidone, 2-vinylpyridine, 3-vinylpyridine, 4-vinylpyridine, triallyl isocyanurate, diallyl isocyanurate, triallylcyanurate, and 1,3,5-triacryloylhexahydro-1,3,5-triazine.

(2-4. Initiator Unsaturated Hydrocarbon Compound (4))

As another method of imparting the functionality to the polymerization terminal group, a polar structure can be provided to the polymerization initiation terminal group by introducing an organic silicon compound, an organic titanium compound, or an organic zirconium compound each having a linear, branched, or cyclic molecular structure, and a terminal modified polymer that cannot be obtained by existent alkylborane polymerization can be obtained. The organic silicon compound, the organic titanium compound and the organic zirconium compound are collectively referred to as "organo-metal compound".

The organo-metal compound is not particularly restricted so long as the compound satisfies the conditions described above and a compound containing an alkoxy group or acetoxy group in the structure is a basic structure of a coupling agent for enhancing the adhesion of the hetero-interface. The coupling agent shows an effect of improving adhesion at the interface between the organic material and the inorganic material and is utilized for bonding of glass fibers, inorganic fillers, metal materials, etc.

Examples of the polymerization terminal group is not particularly restricted so long as the compound has a functional group which can be expected for chemical bond between the inorganic compound and the organic compound and this is an organic silicon compound, an organic titanium compound, and an organic zirconium compound having at least one alkoxy group, acetoxy group, and halogen atom capable of bonding with the inorganic material by hydrolysis. The organic silicon compound is more preferred.

Specific examples of the unsaturated monomer used herein include vinyl trichlorosilane, vinyl triethoxysilane, methacryloxypropyl trimethoxysilane and styryl methoxysilane.

(2-5. Initiator Unsaturated Hydrocarbon Compound (5))

As the unsaturated monomer forming the polymerization initiator according to this embodiment, a multifunctional unsaturated hydrocarbon compound containing at least two unsaturated hydrocarbon groups can be used. So long as the compound is an unsaturated monomer capable of addition reaction (hydroboration) with the borane compound, the structure and the bonding site of the unsaturated hydrocarbon group and the structure of the monomer are not particularly restricted. Polymers of special structures such as multibranched polymers, grafted polymers, and brush-shaped polymers can be prepared by using an unsaturated monomer having a plurality of polymerization initiation points. Such structure can be selected optionally depending on the structure of the unsaturated monomer.

An example of the unsaturated monomer containing two or more unsaturated hydrocarbon groups includes such a multifunctional compound as having one atom (silicon atom, etc.) as a center skeleton and two or more unsaturated hydrocarbon groups are contained to the atom. Multibranched polymers as illustrated in FIGS. 5A to 5C can be prepared by using the monomer. Specific examples of such unsaturated monomer include, for example, tetravinylsilane, tetrallylsilane, and phenyltriallylsilane.

Another example of the unsaturated monomer containing two or more unsaturated hydrocarbon groups includes a polyfunctional compound having a cyclic molecular structure as a center skeleton and containing at least two unsaturated hydrocarbon groups on the side chain of the structure. By using the monomer, the multibranched polymers as illustrated in FIGS. 5A to 5C can be prepared. Specific examples of such unsaturated monomer include, for example, divinylbenzene, trivinylcyclohexane, tribally isocyanurate, triacrylate isocyanurate, diallyl isocyanurate, triallyl cyanurate, and 1.3.5-triacryloylhexahydro-1,3,5-triazine.

Another example of the unsaturated monomer containing two or more unsaturated hydrocarbon groups includes multifunctional compounds having a linear or branched molecular structure and containing at least two unsaturated hydrocarbon groups in the molecular structure. By using the monomer, the multibranched polymer, the grafted type polymer and the brush-shaped polymer as illustrated in FIGS. 5A to 5C can be prepared.

Specific examples of such unsaturated monomers include bifunctional acrylate compounds, bifunctional methacrylate compounds and bifunctional vinyl compounds and, in addition, tetraallyloxyethane, pentaerythritol triallyl ether, pentaerythritol triacrylate, trimethylolpropane triacrylate, trimethylolpropane tetraacrylate, dipentaerythritol hexaacrylate, and trimethylolpropane trimethacrylate.

(3. Unsaturated Hydrocarbon Compound Forming Polymer)

The unsaturated hydrocarbon compound forming the polymer according to the present embodiment (unsaturated monomer) is not particularly restricted so long as the compound has an unsaturated bond and is a radically polymerizable unsaturated monomer. That is, the resin material according to the present embodiment is obtained by radical polymerization of known optional radical polymerizable unsaturated monomers.

In the present description, "unsaturated monomer forming the polymer" is an unsaturated monomer as a repeating unit of a polymeric resin material formed by polymerization of the unsaturated monomer (also referred to simply as "resin material"). For example, an unsaturated monomer forming polystyrene as the resin material is styrene.

Further, it is identical also in a case where the resin material is a copolymer, for example, a block polymer. However, when the copolymer is, for example, a random copolymer, the reacting units described above may not sometimes be generated, but the unsaturated monomer used in the manufacture of the resin material is considered as "unsaturated monomer constituting or forming the resin material" also in such a case.

Such unsaturated monomer includes, for example, unsaturated monomer of low molecular weight having a radically polymerizable functional group such as a vinyl group; and a polymerizing unsaturated monomer of relatively high molecular weight such as an unsaturated polyester and an epoxy vinyl ester. Further, there is no particular restriction also for the structure of the unsaturated monomer such as monofunctional unsaturated monomer not forming by itself a crosslinker structure, and a multifunctional unsaturated monomer having a plurality of polymerizing sites referred to as a crosslinker.

Specific examples of such unsaturated monomers include aromatic vinyl compounds such as styrene, α-methylstyrene, o-methylstyrene, m-methoxy styrene, o-chlorostyrene, m-chlorostyrene, N,N-dimethyl-p-amino styrene, and divinylbenzene; alkyl(meth)acrylates such as methyl(meth)acrylate, ethyl(meth)acrylate, n-propyl acrylate, n-butyl acrylate, 2-ethylhexyl(meth)acrylate, and stearyl(meth)acrylate; unsaturated monocarboxylic acid esters such as methyl crotonate, ethyl crotonate, methyl cinnamate, and ethyl cinnamate; fluoroalkyl(meth)acrylates such as trifluoroethyl (meth)acrylate, pentafluoropropyl(meth)acrylate, and heptafluorobutyl(meth)acrylate; siloxanyl compounds such as trimethyl siloxanyl dimethyl silylpropyl(meth)acrylate, tris (trimethylsiloxyanyl)silylpropyl(meth)acrylate, and di(meth)acryloyl propyl dimethylsilyl ether; monomer or di-(meth)acrylate of alkylene glycol such as ethylene glycol, 1,2-propanediol, 1,3-propanediol, and 1,6-hexanediol; alkoxyalkyl(meth)acrylates such as 2-methoxyethylene (meth)acrylate, 2-ethoxyethyl(meth)acrylate, and 3-ethoxypropyl(meth)acrylate; cyanoalkyl(meth)acrylate such as cyanoethyl(meth)acrylate, and cyanopropyl(meth)acrylate; cyano compounds, such as acrylonitrile and methacrylonitrile; oligo(meth)acrylates of polyhydric alcohols, which are di(meth)acrylates, tri(meth)acrylates, and tetra(meth)acrylates of polyhydric alcohols such as glycerin, 1,2,4-butane triol, pentaerythritol, trimethylol alkanes (number of carbon atoms of the alkane: for example of 1 to 3), tetramethylol alkanes (number of carbon atoms of the alkane, for example, of 1 to 3); hydroxyl alkyl(meth)acrylates such as 2-hydroxyethyl(meth)acrylate, 2-hydroxypropyl(meth)acrylate, and 3-hydroxypropyl(meth)acrylate; hydroxyalkyl esters of unsaturated carboxylic acids such as 2-hydroxyethyl crotonate, 2-hydroxypropyl crotonate, and 2-hydroxypropyl cinnamate; unsaturated alcohols such as (meth)allyl alcohol; unsaturated (mono) carboxylic acids such as (meth)acrylic acid, crotonic acid, and cinnamic acid; and unsaturated polycarboxylic acids (anhydrides) such as (anhydrous)maleic acid, fumaric acid, (anhydrous)itaconic acid, and citraconic acid; as well as monoesters and diesters thereof; epoxy group-containing unsaturated compounds such as allyl glycidyl ether and glycol(meth)acrylate; diene compounds such as butadiene and isoprene; vinyl chloride, vinyl acetate, sodium isoprene sulfonate, cinnamic acid esters, crotonic acid esters, dicyclopentadiene, and ethylidene norbornene.

Among them, preferred examples of the unsaturated monomers applicable to the resin material according to the present embodiment include: aromatic vinyl compounds, alkyl(meth)acrylates, unsaturated monocarboxylic acid esters, fluoroalkyl(meth)acrylates, siloxanyl compounds, mono-(meth)acrylate or di-(meth)acrylates of alkylene glycol, alkoxyalkyl(meth)acrylates, cyanoalkyl(meth)acrylates, acrylonitrile, methacrylonitrile, oligo(meth)acrylates of polyhydric alcohols, hydroxyalkyl(meth)acrylates, hydroxyalkyl esters of unsaturated carboxylic acids, aromatic allyl compounds, hetero ring-containing vinyl compounds, hetero ring-containing allyl compounds, unsaturated alcohols, unsaturated (mono) carboxylic acids, unsaturated polycarboxylic acids or unsaturated polycarboxylic acid anhydrides, monoesters or diesters of unsaturated polycarboxylic acids or unsaturated polycarboxylic acid anhydrides, epoxy group-containing unsaturated compounds, diene compounds, vinyl chloride, vinyl acetate, sodium isoprene sulfonate, cinnamic acid esters, crotonic acid esters, dicyclopentadienyl, and ethylidene norbornene.

Further, the unsaturated monomers may be optionally substituted by arbitrary substituents.

It is not always necessary that the unsaturated monomers are used alone. Accordingly, two or more of them may be used by optional combination and ratio with a view point, for example, of the strength of the resin material (for example, tensile strength, bending strength, etc.), performance such as glass transition temperature and decomposition temperature, and material cost, reactivity, etc.

(4. Process)

The feature of the polymerization method according to the present embodiment resides in that unsaturated monomers of molecular structures different from each other are usable for the unsaturated monomer forming the polymerization initiator and the unsaturated monomer applicable to the resin material. Thus, the molecular structure of the polymerization initiation part and the molecular structure of the constitutional unit forming the main chain of the polymer are different in the polymer, and polymers of special structures such as the terminal modified polymer having functionality imparted to the terminal group, the multibranched polymer, the grafted type (comb-shaped) polymer, and the brush-shaped polymer in which functionality is provided to the terminal group can be prepared.

Another feature of the polymerization method according to the present embodiment resides in that the method has a two-step reaction comprising a polymerization preparation process of preparing a polymerization initiator by addition reaction (hydroboration) of the unsaturated monomer forming the polymerization initiator and the boron compound under an inert gas atmosphere, and a polymer forming process of performing radical addition polymerization to the unsaturated monomer forming a polymer under the presence of oxygen.

Since the polymerization initiator per se is an alkylborane compound prepared by hydroboration, radicals are generated easily by oxygen addition to induce the radical polymerization. On the other hand, since the stage of hydroboration is performed in an inert gas atmosphere, oxidative cleavage and radical generation of the alkylborane subjected to addition reaction do not occur. Accordingly, the process for preparing the polymerization initiator and the process for forming the polymer can be performed separately in the present embodiment and the structure of the polymerization initiator can be designed optionally. For the structure of the polymerization initiator, after hydroboration, precipitation or crystallization may occur occasionally depending on the molecular structure. It is estimated that polymerization initiators are associated each other by physical interaction of the boron compound to cause precipitation. While this is often observed when a multifunctional unsaturated compound is used, they are dissolved again in the solution and can be used for polymerization by properly selecting and adding the solvent. Further, the polymerization initiator can be isolated, for example, by filtration if required.

Another feature of the polymerization method according to the present embodiment resides in that the polymer can be formed all at once without isolation and purification of intermediate products which are usually conducted between the process for preparing the polymerization initiator and the process for forming the polymer. That is, the polymerizing method can be practiced by one pot reaction. The one pot reaction means to perform a plurality of reactions continuously in one reactor.

Usually, in the process for forming the polymerization initiator, a process of isolation and purification is necessary but this is an operation using a great amount of solvent and this is a time consuming and laborious operation. This cannot be said to be a preferred operation with a view point of green chemistry.

On the contrary, in the polymerization method according to the present embodiment, polymerization can be performed while saving the isolation and purification process for intermediate products. Accordingly, the process can be economically excellent with no lowering of yield caused by the isolation and purification process.

A further feature of the polymerization method according to the present embodiment resides in that the process for forming the polymer is living radical polymerization by the formation of the dormant of the boron compound. In the polymerization process, polymerization controllability equivalent to that of the alkylborane polymerization in the existent method can be maintained.

With the view point described above, the polymerization method according to the present embodiment can be said to be a novel living radical polymerization method utilizing borane compound which is performed by a process different from the alkylborane polymerization of the existent method. Further, polymerization initiation site can be selected optionally for the polymerization initiator and the polymer to be prepared by using the present method, and terminal modified polymer of special structure can be prepared. Further, according to the polymerization method of the present embodiment, copolymers can be prepared by adding plural kinds of unsaturated monomers forming the polymer.

In addition, since the polymerization method according to the present embodiment shows living radical polymerizability, random polymerization and block polymerization can be performed optionally by controlling polymerization conditions. Further, functional groups can be changed easily by the dormant species by hydrolysis, proton addition, etc. Known methods can be used therefor and are not restricted by the type of the reaction.

[5. Specific Example for the Application Use of Resin Material]

Then, the application use of the resin material according to this embodiment is to be described in FIG. 6A to FIG. 8 with reference to specific structures.

[5-1. Cable and Cable Coating Material]

Figure 6A:
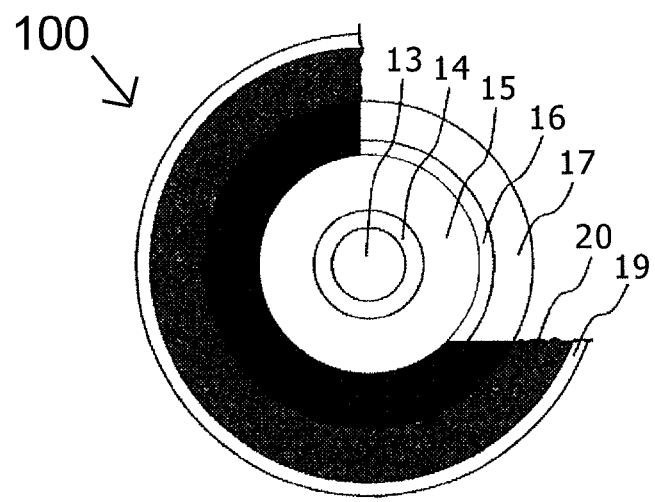
FIG. 6A is a cross sectional view illustrating an example of a cable of applying a polymer according to the present embodiment to a coating layer.
Figure 6B:
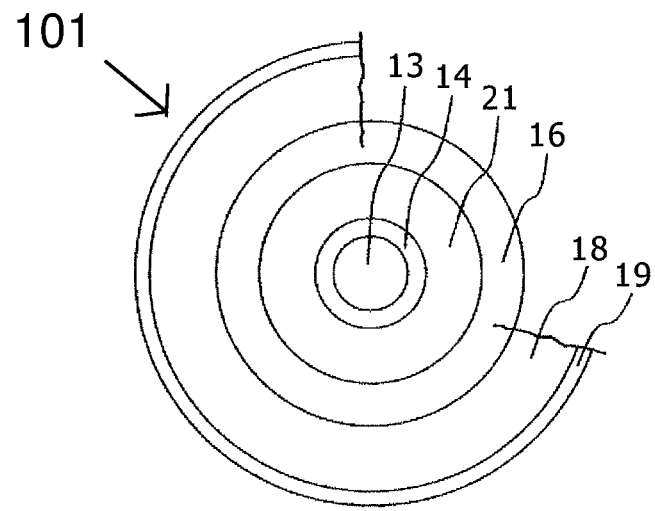
FIG. 6B is a cross sectional view illustrating another example of a cable of applying the polymer according to the present embodiment to a coating layer.

Both of FIGS. 6A and 6B are schematic views illustrating cross sectional structures of cables each having a resin material according to this embodiment. In a cable 100 illustrated in FIG. 6A, the resin material according to this embodiment is used for a coating layer 20. Further, in a cable 101 illustrated in FIG. 6B, the resin material according to this embodiment is used for an insulation layer 21. That is, each of the resin materials according to this embodiment is used as a cable coating material. The terminal modified polymer obtained by the method of FIG. 2 according to this embodiment is a resin having excellent moldability, coatability and flexibility and, in addition, adhesion with inorganic materials can also be improved due to the effect of the terminal modified group.

The cable 100 illustrated in FIG. 6A has a conductor 13, an internal semiconductor layer 14, an insulation layer 15, an external semiconductor layer (adhesion layer) 16, an external semiconductor layer (separable layer) 17, a coating layer 20, and an outer skin layer 19. The material constituting the conductor 13 is not particularly restricted and an optional good conductor such as copper or aluminum can be used. Further, the form of the conductor 13 is not particularly restricted and may be in an optional known form such as a solid (同じ solid) wire, a (twisted) wire, etc. Further, also the cross sectional shape of the conductor 13 is not particularly restricted and can be formed, for example, as a circular shape, a divided circular shape, or a compressed shape.

The material for the internal semiconductor layer 14 and the configuration thereof are not particularly restricted and any known material may be used.

Further, also the material for the insulation layer 15 and the configuration thereof are not particularly restricted, and oil-impregnated paper or oil-impregnated semi-synthetic paper materials, rubber materials, resin materials, etc. can be used. The insulation materials such as rubber materials and resin materials include, for example, ethylene-propylene rubber, butyl rubber, polypropylene, thermoplastic elastomer, polyethylene, crosslinked unsaturated polyethylene, etc. Among them, polyethylene and crosslinked polyethylene are suitable with a view point that they are used generally in insulated cables.

The external semiconductor layer (adhesion layer) 16 is provided with an aim of moderating an intense electric field generated at the periphery of the conductor 13. Material used for the external semiconductor layer (adhesion layer) 16 includes semiconductive resin compositions comprising, for example, resin materials such as styrene-butadiene thermoplastic elastomers, polyester elastomers, and soft polyolefins blended with 20 to 70 mass % of conductive carbon black, and conductive paints with addition of 20 to 70 mass % of conductive carbon. The materials are not particularly restricted so long as they satisfy required performances. The method for forming the external semiconductor layer (adhesion layer) 16 on the surface of the insulation layer 15 is not particularly restricted and includes, for example, continuous extrusion, dipping, spray-coating, and coating depending on the type of members.

The external semiconductor layer (separable layer) 17 is provided with an aim of moderating an intense electric field generated at the periphery of the conductor 13 and protecting the inner layer in the same manner as in the external semiconductor layer (adhesion layer) 16. Further, it may suffice that the layer is easily separated from the external semiconductor layer (adhesion layer) 16 in connection or like other working, and other layer may be interposed therein. Materials used for the external semiconductor layer (separable layer) 17 include, for example, crosslinkable or not-crosslinkable resin composition in which a conductive carbon black is blended by 30 to 100 mass parts based on 100 mass parts of a base material containing at least one rubber material such as soft polyolefin, ethylene-propylene rubber, and butyl rubber, and styrene-butadiene thermoplastic elastomer and polyester elastomer. The materials are not particularly restricted so long as they satisfy the required performance. Further, additives such as graphite, lubricant, metal, and filler such as inorganic filler may be properly incorporated depending on the requirement. A method for forming the external semiconductor layer (separable layer) 17 on the surface of the external semiconductor layer (adhesion layer) 16 is not particularly restricted, and extrusion molding is suitable.

For the coating layer 20, the resin material according to this embodiment is used as described above. Since the resin material according to this embodiment is as has been described above, explanation therefor is to be omitted.

Any known material can be used for the outer skin layer 19, which is not particularly restricted depending on the kind of the material.

The cable 101 illustrated in FIG. 6B is a cable not requiring a separation mechanism of the cable 100 illustrated in FIG. 6A. Accordingly, the cable 101 comprises only one layer of the external semiconductor layer (adhesion layer) 16. Components for the cable 100 and the cable 101 having identical functions carry the same reference sign, for which detailed description is to be omitted.

In the cable 101, the coating layer 18 comprises, for example, a resin material, and comprises any known material. Further, the insulation layer 21 comprises the resin material according to this embodiment described above for which the terminal modified polymer shown in FIG. 2 is used.

Specific examples of both of the cables 100 and 101 have the resin strength and heat resistance equivalent with those of the coating material used so far. In addition, they have appropriate adhesion with the external semiconductor layer and flexibility to external deformation.

[5-2. Mold Sealant, Potting Material, Package for Electronic Part]

The resin material according to this embodiment is applicable for example, also to a mold sealant, a potting material used for the manufacture of a mold sealant (potting material for manufacturing mold sealant), a package for electronic part, etc. Such specific examples are to be described with reference to FIGS. 7A and 7B.

Figure 7A:
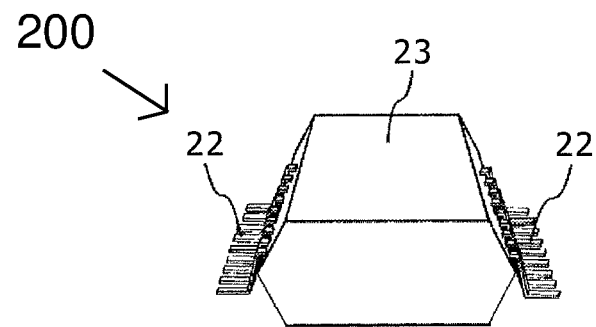
FIG. 7A is a perspective outer view illustrating a package of applying the polymer according to the present embodiment to a mold sealing.
Figure 7B:
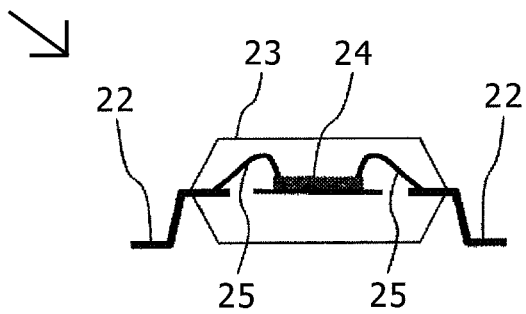
FIG. 7B is a cross sectional view illustrating an inner structure of a package of applying the polymer according to the present embodiment to mold sealing.

FIG. 7A is a perspective view of DIP (Dual Inline Package) 200 as a specific example of a package for electronic part in which the resin material according to this embodiment containing the multibranched polymer illustrated in FIG. 4 is applied as a mold sealant and FIG. 7B is a cross sectional view of the DIP 200 illustrated in FIG. 7A.

The DIP 200 illustrated in FIGS. 7A and 7B includes a semiconductor device 24 disposed over a substrate, lead frames 22, 22 extending outward of a mold sealant 23, and bonding wire 25 for electrically connecting the lead frames 22 and the semiconductor device 24. A portion of the lead frames 22, the semiconductor device 24, a substrate thereof and the bonding wires 25 are sealed by a mold sealant comprising the resin material according to this embodiment containing the multibranched polymer illustrated in FIG. 4.

Each of the lead frame 22 and the bonding frame 25 comprises a good conductor, and comprises specifically, for example, copper or aluminum. Further, the form of the lead frame 22 and the bonding frame 25 can be in any known form, for example, a solid (solid) wire or a twisted wire.

As the shape of the semiconductor device 24, for example, a circular shape, a divided circular shape, a compressed shape, etc. are applicable. Further, the material for forming the semiconductor device 24 is not particularly restricted so long as the material can be sealed by the mold sealant 23.

The mold sealant 23 in the DIP 200 maintains resin strength and heat resistance substantially equal with those of existent materials. In addition, since the mold sealant has a molecular structure of high density inherent to the multibranched structure, it has excellent heat resistance and impact resistance, for example, against fracture caused by impact to the circuit, and against abrupt thermal change accompanying heat generation of the circuit compared with existent chained resins, and improvement of reliability for the entire circuit can be expected. Further, it also has an advantage upon repair treatment that motion of the molecular chain is induced by the heat generated by current supply to the circuit, which promotes moderation and dispersion of the stress.

A method of mold sealing by using the resin material according to this embodiment (mold sealing method) is to be described. Basically, this is performed by forming the resin material in the same manner as in the method of manufacturing the resin material according to this embodiment described above. Specifically, the unsaturated monomer forming the resin material and the radical polymerization initiator according to this embodiment and, optionally, an organic solvent, etc. are mixed and the semiconductor device 24, etc. are sealed by using the obtained mixture. Thus, the semiconductor device 24, etc. can be sealed.

The mixture before polymerization can be utilized also as a potting material for mold sealing (that is, potting material for use in the application of manufacturing the mold sealant). The potting material is used usually by incorporating, for example, an inorganic filler and other resin material, etc. in addition to the components described above.

The potting material for manufacturing the mold sealant and the mold sealant are applicable, for example, to lead frame type package such as SOP (System On Package), QFP (Quad Flat Package), etc.; and a package for electronic parts such as BGA (Ball Grid Array), MCP (Multi Chip Package), etc. in addition to the DIP illustrated in FIG. 7. Further, the object of applying the mold sealant is not restricted only to the semiconductor part but the sealant is applicable also to mold sealing of electronic part of a size larger than that of the semiconductor part.

[5-3. Structural Material]

The resin material according to this embodiment is applicable also to structural materials such as a casing member, a frame member, a panel member, and a model member. Specific examples of them are to be described with reference to FIG. 8.

Figure 8:
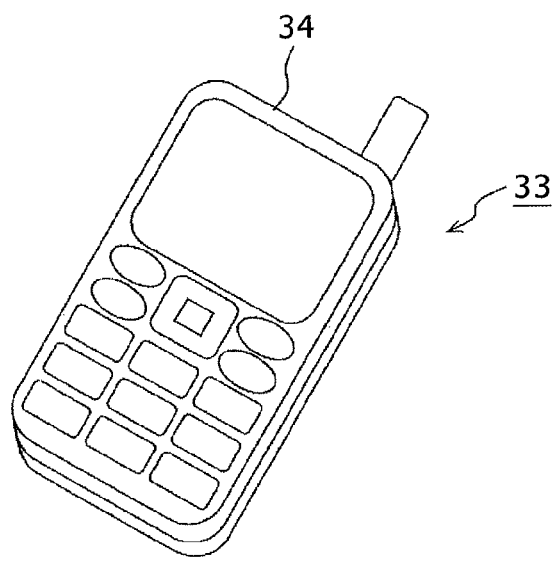
FIG. 8 is a schematic perspective view illustrating a mobile phone using the polymer according to the present embodiment.

FIG. 8 is an example of applying the resin material according to this embodiment as a member for a casing 34 forming a mobile phone 33. The resin material according to this embodiment used for the casing illustrated in FIG. 8 contains the multibranched polymer shown in FIGS. 5A to 5C.

In the mobile phone illustrated in FIG. 8, resin strength and heat resistance equivalent to those of the existent resin material are maintained. In addition, functions such as restoration by dispersion of impact and resiliency, and flexibility can be imparted against friction and impact during manufacture or use of the casing due to a molecular structure of high density and high resiliency inherent to the multibranched structure.

Further, while the casing is mentioned as an example in FIG. 8, the structural material to which the resin material according to this embodiment is applicable is not restricted only to the casing but is applicable in a field where high resiliency and flexibility of the resin material are desired.

[5-4. Other Application Use]

Further, the resin material prepared by this embodiment is excellent in processability and moldability and is applicable, for example, also to a film protection member or a dry film resist in a thin film shape. The resin material maintains resin strength and heat resistance equivalent to those of the existent resin material, and provides a preferred advantage to the film member by imparting the functionality due to the terminal functional group in addition to high resiliency and flexibility.

The present invention is to be described more in details with reference to examples but the invention is not restricted to the following contents but can be practiced with an optional change within a range not impairing the gist of the invention.

(1) Preparation Method of Polymer

A preparation method of a polymer is shown below.

1) An unsaturated hydrocarbon forming an initiator together with a borane compound and a solvent are mixed under heating in a nitrogen gas atmosphere in a 100 mL flask connected with a three-way cock, to prepare a polymerization initiator.

2) The pressure in the flask was reduced to about 1000 Pa and unreacted borane compound was removed under the reduced pressure.

3) The inside of the flask was replaced with a nitrogen gas again, an unsaturated hydrocarbon forming a polymer was added at a normal temperature and normal pressure and a solvent was added optionally.

4) The inside of the flask was stirred while sealing anhydrous air at a normal temperature and normal pressure.

5) After replacing the inside of the flask with a nitrogen gas again, they were heated and mixed to obtain a polymer.

6) After completion of the reaction, a solution containing the polymer (also referred to as "polymer solution") was added into methanol to re-precipitate solid contents and the obtained solid contents were dried under a reduced pressure and then recovered to obtain the polymer.

(2) Evaluation of Molecular Weight of Polymer

For evaluating the molecular weight of the polymer, the molecular weight of the polymer was evaluated by a gel permeation chromatography and, optionally, a multiangle light scattering detector.

For the molecular weight and the mol mass dispersibility, polystyrene-converted values were calculated from measured values by gel permeation chromatography (GPC, GPC-8220GPC manufactured by Tosoh Corp., solvent: N-methylpyrrolidone (NMP), detector: UV light absorption (UV: 254 nm), differential refractometer (RI)). The molecular weight and the molar dispersibility were determined by a calibration curve prepared based on a standard styrene product. The molecular weight distribution was determined according to the ratio (Mw/Mn) between number average molecular weight (Mn) and the weight average molecular weight (Mw) by GPC.

Further, for a polymer of special structure having a plurality of polymerization initiation points, an absolute molecular weight was measured by using a weight average molecular weight (Mw) determined by GPC, and a multi-angle laser light scattering photometer (MALLS), He—Ne laser, DAWN DSP-F manufactured by Wyatt Co.) under the same conditions.

Example 1

(Preparation of Borane-Methyl Methacrylate Polymerization Initiator and Methyl Methacrylate Polymer)

A polymer was prepared by using a borane-THF complex for a boron compound, methyl methacrylate for an unsaturated hydrocarbon to form a polymerization initiator, and methyl methacrylate for an unsaturated hydrocarbon to form a polymer by the following method.

3.0 mL of about 0.9 moL % borane-THF complex solution (about 2.1 mmoL) (manufactured by Tokyo Chemical Industry Co., product code T2346), 0.1 g (1.0 mmoL) of methyl methacrylate (manufactured by Tokyo Chemical Industry Co., product code. M0087), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 2 hours. The polymer solution was subjected to re-precipitation with 100 mL of methanol (manufactured by Wako Pure Chemical Co., product code 131-01826) to obtain a polymer. The yield was 64.2% and Mn was 40,000, Mw was 72,000, and Mw/Mn was 1.8 by GPC measurement.

Example 2

(Preparation of Borane-Styrene Polymerization Initiator and Styrene Polymer)

A polymer was prepared by using a borane-THF complex for a boron compound, styrene for an unsaturated hydrocarbon to form a polymerization initiator, and styrene for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.3 g (3.0 mmoL) of styrene (manufactured by Tokyo Chemical Industry Co., product code. S0095), and 5 mL of tetrahydrofuran (manufactured by Wako Pure Chemical Co., distributor code 208-18535)

were added to a 100 mL flask, heated and stirred in a nitrogen gas atmosphere at 60° C. for one hour to prepare a polymerization initiator.

After reducing the pressure in the flask, 10.4 g (100.0 mmoL) of styrene was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 33.8% and Mn was 31,000, Mw was 50,000, and Mw/Mn was 1.6 by GPC measurement.

Example 3

(Preparation of Borane-Acrylamide Polymerization Initiator and Styrene Polymer)

A polymer was prepared by using a borane-THF complex for a boron compound, acrylamide for an unsaturated hydrocarbon to form a polymerization initiator, and styrene for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.2 g (3.0 mmoL) of acrylamide (manufactured by Tokyo Chemical Industry Co., product code. A1132), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.4 g (100.0 mmoL) of styrene (manufactured by Tokyo Chemical Industry Co., product code 50095) was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 40.1% and Mn was 7,000, Mw was 12,000, and Mw/Mn was 1.6 by GPC measurement.

Example 4

(Preparation of Borane-N,N-Dimethyl Acrylamide Polymerization Initiator and Styrene Polymer)

A polymer was prepared by using a borane-THF complex for a boron compound, N,N-dimethyl acrylamide for an unsaturated hydrocarbon to form a polymerization initiator, and styrene for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.3 g (3.0 mmoL) of N,N-dimethyl acrylamide (manufactured by Tokyo Chemical Industry Co., product code D1091), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.4 g (100.0 mmoL) of styrene (manufactured by Tokyo Chemical Industry Col, product code 50095) was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 55.3% and Mn was 12,000, Mw was 17,000, and Mw/Mn was 1.4 by GPC measurement.

Example 5

(Preparation of Borane-1-Vinyl-2-Pyrrolidone Polymerization Initiator and Methyl Methacrylate Polymer)

A polymer was prepared by using a borane-THF complex for a boron compound, 1-vinyl-2-pyrrolidone for an unsaturated hydrocarbon to form a polymerization initiator, and methyl methacrylate for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.3 g (3.0 mmoL) of 1-vinyl-2-pyrrolidone (manufactured by Tokyo Chemical Industry Co., product code V0026), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with methanol (manufactured by Wako Pure Chemical Co., product code 131-01826) to obtain a polymer. The yield was 54.7% and Mn was 19,000, Mw was 33,000, and Mw/Mn was 1.7 by GPC measurement.

Example 6

(Preparation of Borane-2-Vinylpyridine Polymerization Initiator and Methyl Methacrylate Polymer)

A polymer was prepared by using a borane-THF complex for a boron compound, 2-vinylpyridine for an unsaturated hydrocarbon to form a polymerization initiator, and methyl methacrylate for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.3 g (3.0 mmoL) of 2-vinylpyridine (manufactured by Tokyo Chemical Industry Co., product code V0024), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with methanol (manufactured by Wako Pure Chemical Co., product code 131-01826) to obtain a polymer. The yield was 67.4% and Mn was 21,000, Mw was 29,000, and Mw/Mn was 1.4 by GPC measurement.

Example 7

(Preparation of Borane-Methacrylic Acid Polymerization Initiator and Methyl Methacrylate Polymer)

A polymer was prepared by using a borane-THF complex for a boron compound, methacrylic acid for an unsaturated hydrocarbon to form a polymerization initiator, and methyl methacrylate for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.3 g (3.0 mmoL) of methacrylic acid (manufactured by Tokyo Chemical Industry Co., product code M0079), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with 100 mL of methanol (manufactured by Wako Pure Chemical Co., product code 131-01826) to obtain a polymer. The yield was 48.7% and Mn was 12,000, Mw was 18,000, and Mw/Mn was 1.5 by GPC measurement.

Example 8

(Preparation of Borane-Vinyl Triethoxysilane Polymerization Initiator and Methyl Methacrylate Polymer)

A polymer was prepared by using a borane-THF complex for a boron compound, vinyl triethoxysilane for an unsaturated hydrocarbon to form a polymerization initiator, and methyl methacrylate for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.6 g (3.0 mmoL) of vinyl triethoxysilane (manufactured by Shin-Etsu Silicone Co., product name KBE 1003), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with 100 mL of methanol (manufactured by Wako Pure Chemical Co., product code 131-01826) to obtain a polymer. The yield was 59.9% and Mn was 18,000, Mw was 32,000, and Mw/Mn was 1.8 by GPC measurement.

Example 9

(Preparation of Borane-Vinyl Triethoxysilane Polymerization Initiator and Styrene Polymer)

A polymer was prepared by using a borane-THF complex for a boron compound, vinyl triethoxysilane for an unsaturated hydrocarbon to form a polymerization initiator, and styrene for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.6 g (3.0 mmoL) of vinyl triethoxysilane (manufactured by Shin-Etsu Silicone Co., product name KBE 1003), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.4 g (100.0 mmoL) of styrene (manufactured by Tokyo Chemical Industry Co., product code 50095) was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 42.3% and Mn was 11,000, Mw was 16,000, and Mw/Mn was 1.5 by GPC measurement.

Example 10

(Preparation of Borane-3-Methacryloxy Propyl Trimethoxysilane Polymerization Initiator and Methyl Methacrylate Polymer)

A polymer was prepared by using a borane-THF complex for a boron compound, 3-methacryloxy propyl trimethoxysilane for an unsaturated hydrocarbon to form a polymerization initiator and methyl methacrylate for an unsaturated hydrocarbon to form a polymer by the following method. 9.0 mL of about 0.9 moL % borane-THF complex solution (about 8.1 mmoL) (manufactured by Tokyo Chemical Industry Co., product code T2346), 0.9 g (3.0 mmoL) of 3-methacryloxy propyl trimethoxysilane (manufactured by Shin-Etsu Silicone Co., product name KBM 503), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with ml of methanol (manufactured by Wako Pure Chemical Co., product code 131-01826) to obtain a polymer. The yield was 64.6% and Mn was 22,000, Mw was 37,000, and Mw/Mn was 1.7 by GPC measurement.

Example 11

(Preparation of Borane-p-Styryl Trimethoxysilane Polymerization Initiator and Styrene Polymer)

A polymer was prepared by using a borane-THF complex for a boron compound, p-styryl trimethoxysilane for an unsaturated hydrocarbon to form a polymerization initiator and styrene for an unsaturated hydrocarbon to form a polymer by the following method.

9.0 mL of about 0.9 moL % borane-THF complex solution (about 8.1 mmoL) (manufactured by Tokyo Chemical Industry Co., product code T2346), 0.7 g (3.0 mmoL) of p-styryl trimethoxysilane (manufactured by Shin-Etsu Silicone Co., product name KBM 1403), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.4 g (100.0 mmoL) of styrene (manufactured by Tokyo Chemical Industry Co., product code 50095) was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 49.8% and Mn was 14,000, Mw was 23,000, and Mw/Mn was 1.6 by GPC measurement.

Comparative Example 1

(Preparation of Methyl Methacrylate Polymer not by Way of Hydroboration)

Preparation of a polymer was attempted by the following method by adding isobutyl benzene not having an unsaturated hydrocarbon instead of an unsaturated hydrocarbon to form a polymerization initiator.

9.0 mL of about 0.9 moL % borane-THF complex solution (about 8.1 mmoL) (manufactured by Tokyo Chemical Industry Co., product code T2346), 0.4 g (3.0 mmoL) of isobutyl benzene (manufactured by Tokyo Chemical Industry Co., product code. 10097), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with methanol (manufactured by Wako Pure Chemical Co., product code 131-01826) but precipitation did not occur failing to obtain a polymer.

In view of the above, it is estimated that a polymer was formed by way of hydroboration and the polymer was not formed under the conditions shown in this comparative example. Further, it was found that the borane complex for which addition reaction did not occur was removed by the depressurization treatment described in this example and addition reaction with the unsaturated hydrocarbon to form a polymer did not occur.

Example 12

(Preparation of Borane-Tetraallylsilane Polymerization Initiator and Methyl Methacrylate Polymer)

A polymer was prepared by using a borane-THF complex for a boron compound, tetraallylsilane for an unsaturated hydrocarbon to form a polymerization initiator and methyl methacrylate for an unsaturated hydrocarbon to form a polymer by the following method.

20.0 mL of about 0.9 moL % borane-THF complex solution (about 18.1 mmoL) (manufactured by Tokyo Chemical Industry Co., product code T2346), 0.6 g (3.0 mmoL) of tetraallylsilane (manufactured by Aldrich Co., product No. 86717), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with 100 mL of methanol (manufactured by Wako Pure Chemical Co., product code 131-01826) to obtain a polymer. The yield was 29.8% and Mn by GPC measurement was 9,000, and an absolute molecular weight by MALLS was 25,000.

Example 13

(Preparation of Borane-Pentaerythritol Tetaacrylate Polymerization Initiator and Methyl Methacrylate Polymer)

A polymer was prepared by using a borane-THF complex for a boron compound, pentaerythritol tetraacrylate for an unsaturated hydrocarbon as a polymerization initiator and styrene for an unsaturated hydrocarbon to form a polymer by the following method.

20.0 mL of about 0.9 moL % borane-THF complex solution (about 18.0 mmoL) (manufactured by Tokyo Chemical Industry Co., product code T2346), 1.1 g (3.0 mmoL) of pentaerythritol tetaacrylate (manufactured by Shin-Nakamura Chemical Co., product name A-TMMT), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 6 hours. The polymer solution was subjected to re-precipitation with methanol (manufactured by Wako Pure Chemical Co., product code 131-01826) to obtain a polymer.

The yield was 41.9% and Mw by GPC measurement was 12,000 and an absolute molecular weight by MALLS was 55,000.

Example 14

(Preparation of Borane-Divinyl Benzene Polymerization Initiator and Methyl Methacrylate Polymer)

A polymer was prepared by using a borane-THF complex for a boron compound, divinyl benzene for an unsaturated hydrocarbon to form a polymerization initiator and methyl methacrylate for an unsaturated hydrocarbon to form a polymer by the following method.

10.0 mL of about 0.9 moL % borane-THF complex solution (about 9.0 mmoL) (manufactured by Tokyo Chemical Industry Co., product code T2346), 0.4 g (3.0 mmoL) of divinyl benzene (mixture of 80% divinyl benzene and 20% ethyl vinylbenzene, manufactured by Aldrich Co., product No. 414565), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 4 hours. The polymer solution was subjected to re-precipitation with methanol (manufactured by Wako Pure Chemical Co., product code 131-01826) to obtain a polymer. The yield was 52.8%, Mw by GPC measurement was 17,000 and an absolute molecular weight by MALLS was 50,000.

Example 15

(Preparation of Borane-Diallyl Isocyanurate Polymerization Initiator and Methyl Methacrylate Polymer)

A polymer was prepared by using a borane-THF complex for a boron compound, diallyl isocyanurate for an unsaturated hydrocarbon to form a polymerization initiator and methyl methacrylate for an unsaturated hydrocarbon to form a polymer by the following method.

10.0 mL of about 0.9 moL % borane-THF complex solution (about 9.0 mmoL) (manufactured by Tokyo Chemical Industry Co., product code T2346), 0.6 g (3.0 mmoL) of diallyl isocyanurate (manufactured by Tokyo Chemical Industry Co., product code T0304), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 6 hours. The polymer solution was subjected to re-precipitation with methanol (manufactured by Wako Pure Chemical Co., product code 131-01826) to obtain a polymer. The yield was 44.2%, Mw by GPC measurement was 15,000, and an absolute molecular weight by MALLS was 48,000.

Example 16

(Preparation of Borane-Triallyl Isocyanurate Polymerization Initiator and Methyl Methacrylate Polymer)

A polymer was prepared by using a borane-THF complex for a boron compound, borane-triallyl isocyanurate for an unsaturated hydrocarbon to form a polymerization initiator and methyl methacrylate for an unsaturated hydrocarbon to form a polymer by the following method.

15.0 mL of about 0.9 moL % borane-THF complex solution (about 13.5 mmoL) (manufactured by Tokyo Chemical Industry Co., product code T2346), 0.7 g (3.0 mmoL) of triallyl isocyanurate (manufactured by Tokyo Chemical Industry Co., product code I0279), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator. Since white crystals which were estimated as association of polymerization initiator were precipitated during formation of the polymerization initiator, anhydrous ethanol (manufactured by Wako Pure Chemical Co., product code, 051-06135) was added till the precipitates were dissolved.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 6 hours. The polymer solution was subjected to re-precipitation with methanol (manufactured by Wako Pure Chemical Co., product code 131-01826) to obtain a polymer. The yield was 28.3%, and Mw by GPC measurement was 16,000, and an absolute molecular weight by MALLS was 52,000.

Example 17

(Preparation of Borane-Triallyl Cyanurate Polymerization Initiator and Methyl Methacrylate Polymer)

A polymer was prepared by using a borane-THF complex for a boron compound, triallyl cyanurate for an unsaturated hydrocarbon to form a polymerization initiator, and methyl methacrylate for an unsaturated hydrocarbon to form a polymer by the following method.

15.0 mL of about 0.9 moL % borane-THF complex solution (about 13.5 mmoL) (manufactured by Tokyo Chemical Industry Co., product code T2346), 0.7 g (3.0 mmoL) of triallyl cyanurate (manufactured by Tokyo Chemical Industry Co., product code T0333), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator. Since white crystals estimated as polymerization initiator association were precipitated in the formation of the polymerization initiator, anhydrous ethanol (manufactured by Wako Pure Chemical Co., product code, 051-06135) was added till the precipitates were dissolved.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 90° C. for 6 hours. The polymer solution was subjected to re-precipitation with methanol (manufactured by Wako Pure Chemical Co., product code 131-01826) to obtain a polymer. The yield was 31.2%, Mw by GPC measurement was 13,000, and an absolute molecular weight by MALLS was 46,000.

Example 18

(Preparation of Borane-Trivinyl Cyclohexane Polymerization Initiator and Methyl Methacrylate Polymer)

A polymer was prepared by using a borane-THF complex for a boron compound, borane-trivinyl cyclohexane for an unsaturated hydrocarbon to form a polymerization initiator and styrene for an unsaturated hydrocarbon to form a polymer by the following method.

15.0 mL of about 0.9 moL % borane-THF complex solution (about 13.5 mmoL) (manufactured by Tokyo Chemical Industry Co., product code T2346), 0.5 g (3.0 mmoL) of trivinyl cyclohexane (mixture of isomers manufactured by Tokyo Chemical Industry Co., product code T0899), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.4 g (100.0 mmoL) of styrene was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 45.3%, Mw by GPC measurement was 12,000, and an absolute molecular weight by MALLS was 49,000.

Example 19

(Preparation of Borane-Trimethylolpropane Triacrylate Polymerization Initiator and Methyl Methacrylate Polymer)

A polymer was prepared by using a borane-THF complex for a boron compound, trimethylolpropane triacrylate for an unsaturated hydrocarbon to form a polymerization initiator, and styrene for an unsaturated hydrocarbon to form a polymer by the following method.

15.0 mL of about 0.9 moL % borane-THF complex solution (about 13.5 mmoL) (manufactured by Tokyo Chemical Industry Co., product code T2346), 0.9 g (3.0 mmoL) of trimethylolpropane triacrylate (manufactured by Shin-Nakamura Chemical Co., product name A-TMPT), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.0 g (100.0 mmoL) of methyl methacrylate was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with 100 mL of methanol (manufactured by Wako Pure Chemical Co., product code 131-01826) to obtain a polymer. The yield was 45.1%, and Mw by GPC measurement was 14,000, and an absolute molecular weight by MALLS was 48,000.

Example 20

(Preparation of Borane-Poly-1,2-Butadiene Polymerization Initiator and Styrene Polymer)

A polymer was prepared by using a borane-THF complex for a boron compound, poly-1,2-butadiene for an unsaturated hydrocarbon to form a polymerization initiator, and styrene for an unsaturated hydrocarbon to form a polymer by the following method.

10.0 mL of about 0.9 moL % borane-THF complex solution (about 9.0 mmoL) (manufactured by Tokyo Chemical Industry Co., product code T2346), 0.3 g of poly-1,2-butadiene (1,2-butadiene repeating unit corresponding to about 4.0 mmoL) (manufactured by JSR Co., JSR-RB-820), 1 mL of toluene (manufactured by Wako Pure Chemical Co., distributor code 20-1344), and 5 mL of tetrahydrofuran (manufactured by Wako Pure Chemical Co., distributor code 208-18535) were added to a 100 mL flask, heated and stirred in a nitrogen gas atmosphere at 60° C. for one hour to prepare a polymerization initiator.

After reducing the pressure in the flask, 10.4 g (100.0 mmoL) of styrene (manufactured by Tokyo Chemical Industry Co., product code 50095) was further added in a nitrogen gas atmosphere and the inside of the flask was stirred for 0.5 hours while sealing anhydrous air at a room temperature and a normal pressure. After completing the stirring, the inside of the system was replaced with a nitrogen gas again and then polymerization was performed at 50° C. for 8 hours. The polymer solution was subjected to re-precipitation with methanol (manufactured by Wako Pure Chemical Co., product code 131-01826) to obtain a grafted styrene polymer. The yield was 32.1%, and Mw of poly-1,2-butadiene by GPC measurement was 90,000 and an absolute molecular weight by MALLS was 120,000 before graft polymerization. On the other hand, Mw by GPC measurement was 100,000 and an absolute molecular weight by MALLS was 340,000 after graft polymerization, to confirm remarkable increase of the absolute molecular weight. Further, according to GPC chart after polymerization, characteristic side peaks were not confirmed and the presence of oligomer components was not confirmed. In addition, according to $^1$H NMR (GSX-400 (400 MHz) manufactured by JEOL Ltd.), elimination of the unsaturated bond and introduction of styrene-derived aromatic hydrocarbon were confirmed.

Example 21

(Formation of Polymerization Initiator by Hydroboration)

A polymerization initiator was prepared by mixing borane-THF complex for a boron compound and a triallyl cyanurate for an unsaturated hydrocarbon to form a polymerization initiator. The polymerization initiator was subjected to stability conformation and structural analysis by NMR.

18.0 mL of about 0.9 moL % borane-THF complex solution (manufactured to Tokyo Chemical Industry Co., product code T2346) (about 16.2 moL), 2.1 g (3.0 mmoL) of triallyl cyanurate (manufactured by Tokyo Chemical Industry Co., product code T0333) and 5 mL of tetrahydrofuran (manufactured by Wako Pure Chemical Co., distributor code 208-18535) were added to a 100 mL flask and heated and stirred in a nitrogen gas atmosphere at 60° C. for 1 hour to prepare a polymerization initiator. Precipitates formed upon formation of the polymerization initiator (polymerization initiator) were isolated by filtration in air.

The isolated product was rapidly dissolved in methanol. For the products, insolubilization along with formation of a three-dimensional network structure such as swelling or gelation was not confirmed. Further, the precipitates were dissolved in deuterided dimethylsulfoxide (manufactured by Sigma Aldrich Co., product code 151874-5G) and $^{11}$B-NMR was measured.

Figure 9:
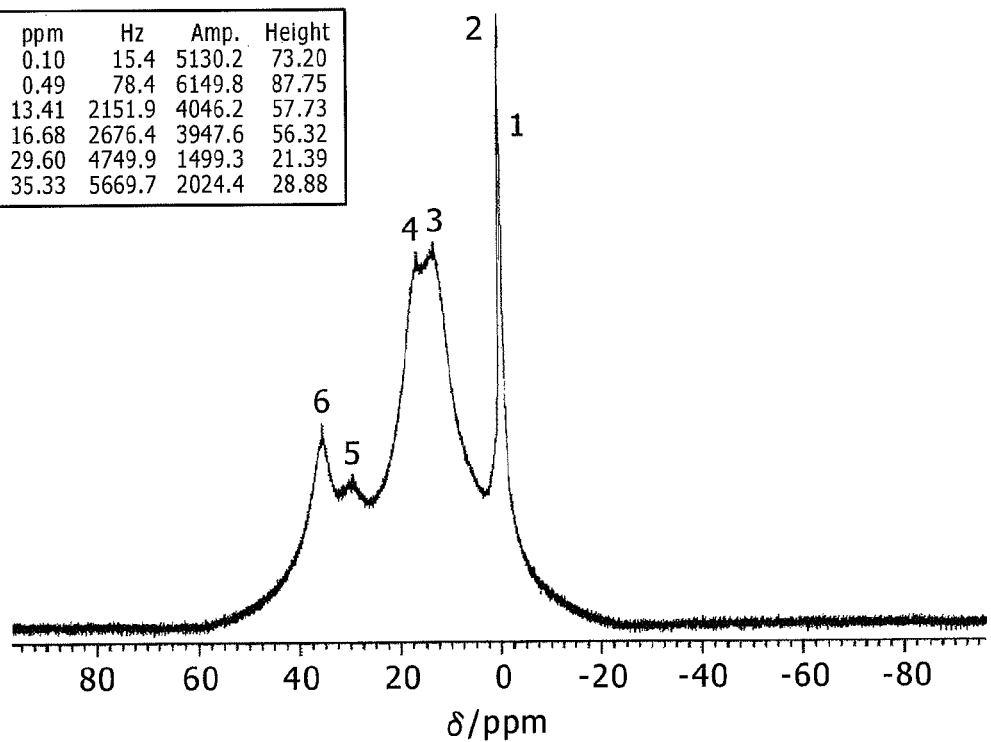
FIG. 9 is a graph showing $^{11}$B-NMR spectrum of a polymerization initiator prepared by hydroboration reaction shown in Example 21.

FIG. 9 shows the result of $^{11}$B-NMR measurement.

In addition to the peaks derived from $BH_3$-THF complex (0 to 0.5 ppm), formation of 1-substituted hydroboration product (B—(OR')$_2$—R", 13.0 to 17.0 ppm) in which one molecule of the monomer was added to borane and 2-substituted hydroboration product (B—(OR')—R"—R'", 29.0 to 35.0 ppm) in which two molecules of the monomer were added to borane were also confirmed.

The result described above suggested that the isolated precipitates are borane adduct formed by hydroboration and crystals thereof can be present stably also in air at normal temperature and normal pressure.

Further, for one g of the isolated polymerization initiator, methyl methacrylate was further added by 10.0 g (100.0 mmoL) and the inside of flask was stirred for 0.5 hours. After completing stirring, the inside of the system was again substituted with a nitrogen gas and then polymerization was performed at 90° C. for 6 hours. The polymer solution was precipitated with methanol (manufactured by Wako Pure Chemical Co., product code 131-01826) to obtain a polymer. Mw by GPC measurement was 9,000 and an absolute molecular weight by MALLS was 31,000.

Example 22

(Behavior of Polymerization Initiator in Heating Under Conditions without Adding Unsaturated Hydrocarbon Forming a Polymer)

1 mL of tetrahydrofuran was added to 1 g of the polymerization initiator isolated in Example 21, anhydrous ethanol (manufactured by Wako Pure Chemical Co., product code 051-06135) was added till the precipitates were dissolved and the inside of the system was replaced with a nitrogen gas again. Then, polymerization was performed at 90° C. for 6 hours. The polymer solution with was subjected to re-precipitation with ethanol (manufactured by Wako Pure Chemical Co., product code 131-01826) but precipitation did not occur failing to obtain a polymer.

In view of the above, it is estimated that the polymer was formed only by the addition of the unsaturated hydrocarbon forming the polymer and the polymer was not formed under the conditions shown in this example. Further, it was found that polymer terminals causing addition reaction by hydroboration do not react each other and the polymerization initiator can be present stably in the system also under an oxygen atmosphere.

Example 23

(Behavior of Polymerization Initiator in Heating in which the Amount of the Borane Compound is Equal with or Less than the Amount of Unsaturated Hydrocarbon)

The stability of the polymerization initiator when the addition amount of the boron compound was equal with or less than the amount of the unsaturated hydrocarbon instead of the conditions in Example 22 was demonstrated by the following method.

A polymerization initiator prepared by using a borane-THF complex for the boron compound and triallyl cyanurate for the unsaturated hydrocarbon to form the polymerization initiator was subjected to stability confirmation and structural analysis by NMR.

1.0 mmoL of about 9 moL % borane-THF complex solution (manufactured to Tokyo Chemical Industry Co., product code T2346) (about 0.9 mmoL), 2.1 g (3.0 mmoL) of trially cyanurate (manufactured by Tokyo Chemical Industry Co., product code T0333) and 5 mL of tetrahydrofuran (manufactured by Wako Pure Chemical Co., distributor code 208-18535) were added into a 100 mL flask and heated and stirred at 60° C. for one hour in a nitrogen gas atmosphere to prepare a polymerization initiator. After stirring the inside of the flask for 0.5 hours while sealing anhydrous air at a normal temperature and a normal pressure, the inside of the system was again replaced with a nitrogen gas and heated to 60° C.

As a result, gel-like precipitates insoluble to a solvent were precipitated. The precipitates were insoluble to an organic solvent such as toluene, methanol, and tetrahydrofuran and a polymer different from that in Example 22 was formed. It is estimated that the not hydroborated unsaturated hydrocarbon and polymerization initiation terminal were bonded by the reaction to form three-dimensional network gelled crosslinked product. Further, it was found that the polymerization initiator could not be present stably in the system under an oxygen atmosphere when addition reaction of the unsaturated hydrocarbon caused by hydroboration did not proceed sufficiently.

Comparative Example 2

(Preparation of Triallyl Cyanurate-Methyl Methacrylate Polymer Using Alkylborane Initiator)

A polymer was prepared by using an alkylborane for the boron compound, and triallyl cyanurate for the unsaturated hydrocarbon to form the polymerization initiator, and methyl methacrylate for the unsaturated hydrocarbon to form the polymer by the following method with reference to the method of Example 17.

10.0 mL of about 1 moL/L triethylborane-THF complex solution (manufactured by Tokyo Chemical Industry Co., product code T2346) (about 10.0 mmoL), 0.7 g (3.0 mmoL) of triallyl cyanurate (manufactured by Tokyo Chemical Industry Co., product code T1984) and 5 mL of tetrahydrofuran (manufactured by Wako Pure Chemical Co., distributor code 208-18535) were added into a 100 mL flask and heated and stirred in a nitrogen gas atmosphere at 60° C. for one hour. 10.0 g (100.0 mmoL) of methyl methacrylate was further added in a nitrogen gas atmosphere and the inside of flask was stirred for 0.5 hours while sealing anhydrous air at a normal temperature and normal pressure. After completing stirring, when the inside of the system was substituted again with a nitrogen gas and then heated at 90° C., gel-like precipitates insoluble to solvent were precipitated.

The precipitates were insoluble to an organic solvent such as toluene, methanol, and tetrahydrofuran to form a polymer different from that of Example 17. It is estimated that the not hydroborated unsaturated hydrocarbon and the polymerization initiation terminal are bonded by the reaction to form three-dimensional network-like gelled crosslinked products. It is estimated that the reaction caused random copolymerization between triallyl cyanurate and methyl methacrylate to form the three-dimensional gelled crosslink product. As a result, it has been found that a polymer of special structure such as terminal modified polymer, multibranched polymer or grafted type polymer cannot be prepared as in the present embodiment by polymerization using the alkylborane initiator according to the prior art.

Example 24

(Cable and Cable Coating Material Using the Resin Material of the Invention)

Example 24 is an example of a cable and a cable coating member using a terminal-modified resin material.

FIG. 6A shows an example of a cable of applying the terminal modified resin material of Example 5 to the coating layer of the cable and FIG. 6B shows an example of applying the terminal-modified resin material of Example 8 to an insulation layer inside the cable.

For the material of the conductor 13 in this example, an optional good conductor such as copper or aluminum is used. Further, the conductor 13 may be in a known form such as a solid (solid) wire or a twisted wire. Further, a circular, divided circular, or compressed shape is used for the shape of the conductor 13.

For the internal semiconductor layer 14 and the outer skin layer 19 in FIG. 6A, optional material may be used and the layer is not particularly restricted by the type of the material. Further, any material may be used for the insulation layer 15 so long as it can provide an insulative coating to the conductor 13 and materials of oil immersed paper, oil immersed semi-synthetic paper, rubber materials, resin material, etc. are mainly used. The insulative materials such as rubber and resin materials include, for example, ethyl-propylene rubber, butyl rubber, polypropylene, thermoplastic elastomer, polyethylene, and crosslinked unsaturated polyethylene (crosslinked polyethylene). Particularly, polyethylene and crosslinked polyethylene are the mainstream of the insulative cable and are more preferred examples.

The external semiconductor layer (adhesion layer) 16 is provided with an aim of moderating an intense electric field generated at the periphery of the conductor 13. Material used for the external semiconductor layer (adhesion layer) 16 includes semiconductive resin compositions comprising, for example, resin materials such as styrene-butadiene thermoplastic elastomers, polyester elastomers, and soft polyolefins blended with 20 to 70 mass % of conductive carbon black, and conductive paints with addition of 20 to 70 mass % of conductive carbon, with no particular restriction so long as the material satisfies required performances. The method for forming the external semiconductor layer (adhesion layer) 16 on the surface of the insulation layer is not particularly restricted and includes, for example, continuous extrusion, dipping, spray-coating, and coating depending on the type of the member.

The external semiconductor layer (separable layer) 17 is provided with an aim of moderating an intense electric field generated at the periphery of the conductor 13 and protecting the inner layer in the same manner as in the external semiconductor layer (adhesion layer) 16. Further, it may suffice that the layer is easily separated from the external semiconductor layer (adhesion layer) 16 in connection or like other working, and other layer may be interposed therein. The material used for the external semiconductor layer (separable layer) 17 includes, for example, crosslinkable or not-crosslinkable resin composition in which conductive carbon black is blended by 30 to 100 mass parts based on 100 mass parts of a base material containing at least one of soft polyolefins, rubber materials such as ethylene-propylene rubber and butyl rubber, styrene-butadiene thermoplastic elastomers, and polyester elastomers, with no particular restriction so long as the required performance is satisfied. Further, additives such as graphite, lubricant, metal, and filler such as inorganic filler may be properly incorporated depending on the requirement. A method for forming the external semiconductor layer (separable layer) 17 on the surface of the insulative layer (adhesion layer) 16 is not particularly restricted and mainly, extrusion molding is a preferred example.

Further, optional material may be used for the internal semiconductor layer 14, the coating layer 18, and the outer skin layer 19 in FIG. 6B and they are not particularly restricted by the type of the member. This is intended for an example not requiring a separation mechanism as in FIG. 6A and consisting only one external semiconductor layer 16 (adhesion layer).

Any of the examples has resin strength and heat resistance equivalent with those of coating materials used so far and, in addition, has appropriate adhesion with the external semiconductor layer and flexibility against external deformation. In addition, self-repairability can be provided to the coating material by applying an appropriate molding treatment to provide a state of maintaining dormant species. Thus, against damages of the resin material such as scratches due to friction with the outside and between cables to each other and occurrence of micro cracks due to abrupt thermal change during manufacture and use of the cable, the resin strength and the heat resistance at the damaged portion can be maintained to a performance equivalent with those before undergoing damages, by supplying a repairing agent from the outside or inside and applying appropriate repairing treatment.

Example 25

(Mold Sealing, Mold Sealant, Potting Material, and Package Using the Resin Material of the Invention)

Example 25 is an example of mold sealing and mold sealant for electronic part using a multibranched resin material.

FIG. 7A illustrates an appearance of a package (DIP: Dual Inline Package) of applying the resin material incorporating the multibranched resin material of Example 18 and having a repairing function to mold sealing and FIG. 7B illustrates a structure inside the package.

For the material of the conductor (lead frame 22) and the bonding wire 25 in this example, an optional good conductor such as copper or aluminum is used. Further, the conductor may be in a known form such as a solid (solid) wire and a twisted wire. Further, a circular, a divided circular, compressed form, etc. are used for the shape of the conductor. Further, any semiconductor device 24 can be used with no particular restriction so long as it comprises a material suitable to sealing by the package.

In the mold sealing and the package of this example, fluidity of the polymer can be reduced to less than that of the existent chained resin to obtain a resin material of excellent moldability by providing a multibranched structure for the polymer while maintaining the resin strength and the heat resistance equivalent to those of the existent materials. In addition, against the damage of the resin material such as fracture due to impact to the circuit and occurrence of micro cracks due to abrupt thermal change accompanying the heat generation of the circuit, it is possible to maintain the resin strength and the heat resistance for the damaged portion at such a performance equal with those before undergoing damages, by supplying a restoring agent from the inside of the resin material and applying appropriate repairing treatment by providing a state of maintaining the dormant species by an appropriate molding treatment. Upon repair, an effect of promoting repair can be obtained by heat generation of the circuit.

Upon mold sealing in this example, mold sealing is performed by polymerization by compositing the polymerization initiator and the monomer constituting the resin material of the invention with an organic solvent, etc. and composited products before polymerization can be used as the potting material for mold sealing. The potting material can be used in admixture with an inorganic filler or other resin material. Further, the potting material can be applied to package for electronic parts, for example, as a lead frame type package such as SOP (System On Package) or QFP (Quad Flat Package) and BGA (Ball Grid Array), MCP (Multi Chip Package) in addition to DIP. Further, the object of mold sealing is not restricted to the semiconductor part but this is applicable also to mold sealing for an electronic part larger than the semiconductor part.

Example 26

(Structural Material Containing the Resin Material of the Invention)

Example 26 is an example of a structural material for a casing using the resin material having a repairing function.

FIG. 8 illustrates an example of a casing made of the resin material of applying the resin material having the grafted structure shown in Example 20 to a structural material.

By applying the polymer of the special structure, the resin strength and the heat resistance equivalent to those of the extent material are maintained and restoration due to dispersion of impact and resiliency can be provided against scratches or impact, for example, during manufacture or use of the casing by the molecular structure having a high density and high resiliency inherent to the multibranched structure. Further, while the casing is shown as an example in FIG. 8, the structural material to which the resin material according to this embodiment is applicable is not restricted to the casing but the material is applicable to a field in which the high elasticity and flexibility are desired for the resin material.

According to the invention, the structure of the polymerization initiation terminal can be freely selected and controlled, for example, by introducing only one molecule of the polymerization initiation terminal selectively, which could not be attained in the prior art, while maintaining the excellent controllability of the alkyl borane system in the prior art on radical polymerization. For example, a terminal modified polymer in which functionality is imparted to the terminal group can be prepared. Further, a polymerization initiator having a plurality of polymerization initiation points can be prepared and polymers of special structure such as a multibranched polymer, a grafted type (comb-shaped) polymer, and brush-shaped polymer can be prepared.

LIST OF REFERENCE SIGNS 1 polymerization initiation part
2, 6, 10 radical polymerization part
3, 7, 11 radical polymerization terminal
4, 8, 12 boron-containing oxygen-centered radical
5, 9 polymerization initiation terminal
13 conductor
14 internal semiconductor layer
15 insulation layer
16, 17 external semiconductor layer
18 coating layer
19 outer skin layer
20 coating layer
21 insulation layer
22 lead frame
23 mold sealant
24 semiconductor device
25 bonding wire
33 mobile telephone
34 casing

The invention claimed is:

1. A polymerization initiator which is a compound prepared by addition reaction of a boron compound and a first unsaturated hydrocarbon compound, and oxidized by addition of oxygen to generate a radical, wherein the radical has a function of reacting with a second unsaturated hydrocarbon to form a polymer, wherein the first unsaturated hydrocarbon compound contains at least one molecular structure selected from the group consisting of ether bond, ester bond, urethane bond, amide bond, thioester bond, carbonyl group, carboxyl group, amino group, alkylamino group, dialkylamino group, pyridyl group, pyrrolidyl group, isocyanuric acid ester skeleton, cyanuric acid ester skeleton, hexahydrotriazine skeleton, maleimide skeleton, and imidazole skeleton, and the boron compound contains at least one molecular skeleton selected from the group consisting of an organic silicon skeleton, an organic titanium skeleton, and an organic zirconium skeleton each having a linear, branched or cyclic molecular structure, and has a function of forming a polymerization initiation terminal radical containing the molecular skeleton by oxidation.

2. The polymerization initiator according to claim 1, wherein the first unsaturated hydrocarbon compound is acrylamide, N, N-dimethyl acrylamide, 1-vinyl-2-pyrrolidone, 2-vinylpyridine, methacrylic acid, vinyl triethoxysilane, 3-methacryloxypropyl trimethoxysilane, p-styryl trimethoxysilane, tetraallyl silane, pentaerythritol tetraacrylate, divinyl benzene, diallyl isocyanurate, triallyl isocyanurate, triallyl cyanurate, trivinyl cyclohexane, trimethylol propane triacrylate, or poly-1,2-butadiene.

3. The polymerization initiator according to claim 1, wherein the boron compound contains one or more atoms selected from the group consisting of oxygen, nitrogen, phosphorus, sulfur, and halogen, has a linear, branched, or cyclic heteroatom-containing alkyl structure, and forms a polymerization initiation terminal radical containing the heteroatom-containing alkyl structure by oxidation.

4. The polymerization initiator according to claim 1, wherein the boron compound has at least two alkylborane structures bonded to one atom as a center skeleton, at least two alkyl borane structures bonded to the side chain of a cyclic molecular structure as a center skeleton, or a linear or branched molecular structure as a center skeleton, has at least two alkylborane structures in the molecular structure, and has a function of forming at least two polymerization initiation terminal radicals by oxidation.

5. A method for forming a polymer including, using a mixture containing the polymerization initiator according to claim 1 and the second unsaturated hydrocarbon compound, generating the radical by oxidation of the polymerization initiator, and adding the radical to the second unsaturated hydrocarbon compound, thereby forming the polymer.

6. The method for forming the polymer according to claim 5, wherein the molecule of the first unsaturated hydrocarbon compound contains at least one configuration selected from the group consisting of a configuration containing at least two unsaturated hydrocarbon groups and having one atom as a center skeleton with at least two unsaturated hydrocarbon groups bonded to the atom, a configuration having a cyclic molecular structure as a center skeleton with at least two unsaturated hydrocarbon groups contained on the side chain of the molecular structure, a configuration having a linear or branched molecular structure with at least two unsaturated hydrocarbon groups contained in the molecular structure, and a configuration containing an organic silicon compound, an organic titanium compound, or an organic zirconium compound each having a linear, branched, or cyclic molecular structure.

7. The method for forming the polymer according to claim 5, wherein the method further includes a step of adding the first unsaturated hydrocarbon compound to the boron compound thereby preparing the polymerization initiator, the first unsaturated hydrocarbon compound and the second unsaturated hydrocarbon compound are different compounds, and the molecular structure at the polymerization initiation terminal of the first unsaturated hydrocarbon compound and the molecular structure of a configurational unit configuring the main chain of the polymer formed by the polymerization of the second unsaturated hydrocarbon compound are different.

8. A polymer prepared from the polymerization initiator and the second unsaturated hydrocarbon compound by the forming method according to claim 5.

9. The polymer according to claim 8 comprising a polymerization initiation part, a polymerization terminal part and a main chain disposed between them, in which at least one molecular structure in the polymerization initiation part and the polymerization terminal part and a molecular structure of repeating unit forming the main chain are different, and the boron compound forms a growth terminal group.

10. The polymer according to claim 8, wherein the second unsaturated hydrocarbon group is one or more unsaturated monomers selected from the group consisting of aromatic vinyl compounds, aromatic allyl compounds, heterocyclic ring-containing vinyl compounds, heterocyclic ring-containing allyl compounds, alkyl(meth)acrylates, unsaturated monocarboxylic acid esters, fluoroalkyl(meth)acrylates, siloxanyl compounds, mono-(meth)acrylate and di-(meth) acrylates of alkylene glycols, alkoxyalkyl(meth)acrylates, cyanoalkyl(meth)acrylates, acrylonitrile and methacrylonitrile; oligo(meth)acrylates and hydroxyalkyl(meth)acrylates of polyhydric alcohols, hydroxyalkyl esters of unsaturated carboxylic acids, unsaturated alcohols, unsaturated(mono) carboxylic acids, unsaturated polycarboxylic acids, and unsaturated polycarboxylic acid anhydrides; monoesters and diesters of unsaturated polycarboxylic acids or unsaturated polycarboxylic acid anhydrides; epoxy group-containing unsaturated compounds, diene compounds, vinyl chloride, vinyl acetate, sodium isoprene sulfonate, cinnamic acid esters, crotonic acid esters, dicyclopentadienyl, and ethylidene norbornene.

11. The polymer formed by using the polymerization initiator according to claim 1, wherein the polymer comprises a polymerization initiation part, a polymerization terminal part, and a main chain disposed between them in which at least one molecular structure of the polymerization initiation part and the polymerization terminal part has a linear, branched, or cyclic molecular structure containing one or more atoms selected from the group consisting of oxygen, nitrogen, phosphorus, sulfur, and halogen, or at least one molecular structure selected from the group consisting of ether bond, ester bond, urethane bond, amide bond, thioester bond, carbonyl group, carboxyl group, amino group, alkylamino group, dialkylamino group, pyridyl group, pyrrolidyl group, isocyanuric acid ester skeleton, cyanuric acid ester skeleton, hexahydrotriazine skeleton, maleimide skeleton, and imidazole skeleton, or at least one molecular skeleton selected from the group consisting of an organic silicon skeleton, an organic titanium skeleton, and an organic zirconium skeleton each having a linear, branched, or cyclic molecular structure.

12. A polymer formed by using the polymerization initiator according to claim 1, and comprising a molecular structure having one atom as a center skeleton and at least two chain growth parts bonded to the atom, or a molecular structure having one cyclic part as a center skeleton and at least two chain growth parts bonded to the cyclic part, or a molecular structure having a chained part or a branched part and having at least two chain growth parts bonded to the chain part or the branched part.

13. A cable coating material using a polymer according to claim 8.

14. A cable using the cable coating material according to claim 13.

15. A mold sealant using the polymer according to claim 8.

16. A package for an electronic part using the mold sealant according to claim 15.

* * * * *